United States Patent
Korlach et al.

(10) Patent No.: US 7,033,764 B2
(45) Date of Patent: *Apr. 25, 2006

(54) METHOD FOR SEQUENCING NUCLEIC ACID MOLECULES

(75) Inventors: Jonas Korlach, Ithaca, NY (US); Watt W. Webb, Ithaca, NY (US); Michael Levene, Ithaca, NY (US); Stephen Turner, Ithaca, NY (US); Harold G. Craighead, Ithaca, NY (US); Mathieu Foquet, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/014,015

(22) Filed: Dec. 15, 2004

(65) Prior Publication Data

US 2005/0158761 A1    Jul. 21, 2005

Related U.S. Application Data

(63) Continuation of application No. 09/572,530, filed on May 17, 2000.

(60) Provisional application No. 60/134,827, filed on May 19, 1999.

(51) Int. Cl.
  *C12Q 1/68*   (2006.01)
  *C12M 3/00*   (2006.01)
  *G01N 21/00*  (2006.01)
  *C07H 21/02*  (2006.01)

(52) U.S. Cl. .................. 435/6; 435/183; 435/287.2; 436/94; 436/164; 536/23.1; 536/24.33; 536/25.32

(58) Field of Classification Search ................ 435/6, 435/91.1, 91.2, 183, 287.2; 536/23.1, 24.31, 536/24.33, 25.72; 436/94, 164
See application file for complete search history.

(56) References Cited

U.S. PATENT DOCUMENTS 4,994,373 A    2/1991    Stavrianopoulos et al.

(Continued)

*Primary Examiner*—Bradley L. Sisson
(74) *Attorney, Agent, or Firm*—Wilson Sonsini Goodrich & Rosati

(57) ABSTRACT

The present invention is directed to a method of sequencing a target nucleic acid molecule having a plurality of bases. In its principle, the temporal order of base additions during the polymerization reaction is measured on a molecule of nucleic acid, i.e. the activity of a nucleic acid polymerizing enzyme on the template nucleic acid molecule to be sequenced is followed in real time. The sequence is deduced by identifying which base is being incorporated into the growing complementary strand of the target nucleic acid by the catalytic activity of the nucleic acid polymerizing enzyme at each step in the sequence of base additions. A polymerase on the target nucleic acid molecule complex is provided in a position suitable to move along the target nucleic acid molecule and extend the oligonucleotide primer at an active site. A plurality of labelled types of nucleotide analogs are provided proximate to the active site, with each distinguishable type of nucleotide analog being complementary to a different nucleotide in the target nucleic acid sequence. The growing nucleic acid strand is extended by using the polymerase to add a nucleotide analog to the nucleic acid strand at the active site, where the nucleotide analog being added is complementary to the nucleotide of the target nucleic acid at the active site. The nucleotide analog added to the oligonucleotide primer as a result of the polymerizing step is identified. The steps of providing labelled nucleotide analogs, polymerizing the growing nucleic acid strand, and identifying the added nucleotide analog are repeated so that the nucleic acid strand is further extended and the sequence of the target nucleic acid is determined.

24 Claims, 10 Drawing Sheets

U.S. PATENT DOCUMENTS

| | | | |
|---|---|---|---|
| 5,200,313 | A | 4/1993 | Carrico |
| 5,302,509 | A | 4/1994 | Cheeseman |
| 5,403,708 | A | 4/1995 | Brennan et al. |
| 5,405,747 | A | 4/1995 | Jett et al. |
| 5,470,710 | A | 11/1995 | Weiss et al. |
| 5,547,835 | A | 8/1996 | Koster |
| 5,601,982 | A | 2/1997 | Sargent et al. |
| 5,620,854 | A | 4/1997 | Holzrichter et al. |
| 5,631,134 | A | 5/1997 | Cantor |
| 5,646,264 | A | 7/1997 | Glazer et al. |
| 5,661,028 | A | 8/1997 | Foote |
| 5,677,196 | A | 10/1997 | Herron et al. |
| 5,688,648 | A | 11/1997 | Mathies et al. |
| 5,695,934 | A | 12/1997 | Brenner |
| 5,703,222 | A * | 12/1997 | Grossman et al. ......... 536/24.3 |
| 5,846,727 | A | 12/1998 | Soper et al. |
| 5,858,671 | A | 1/1999 | Jones |
| 5,922,591 | A | 7/1999 | Anderson et al. |
| 5,961,923 | A | 10/1999 | Nova et al. |
| 6,004,744 | A | 12/1999 | Goelet et al. |
| 6,027,890 | A | 2/2000 | Ness et al. |
| 6,048,690 | A | 4/2000 | Heller et al. |
| 6,210,896 | B1 | 4/2001 | Chan |
| 6,221,592 | B1 | 4/2001 | Schwartz et al. |
| 6,232,075 | B1 | 5/2001 | Williams |
| 6,255,083 | B1 | 7/2001 | Williams |
| 6,263,286 | B1 | 7/2001 | Gilmanshin et al. |
| 6,280,939 | B1 * | 8/2001 | Allen ............................ 435/6 |
| 6,306,607 | B1 | 10/2001 | Williams |
| 6,355,420 | B1 | 3/2002 | Chan |
| 6,399,335 | B1 | 6/2002 | Kao et al. |
| 6,403,311 | B1 | 6/2002 | Chan |
| 6,485,944 | B1 | 11/2002 | Church et al. |
| 6,524,829 | B1 | 2/2003 | Seeger |
| 2001/0014850 | A1 | 8/2001 | Gilmanshin et al. |
| 2002/0025529 | A1 | 2/2002 | Quake et al. |
| 2002/0164629 | A1 | 11/2002 | Quake et al. |
| 2003/0064366 | A1 | 4/2003 | Hardin et al. |
| 2003/0186255 | A1 | 10/2003 | Williams et al. |
| 2003/0194740 | A1 | 10/2003 | Williams et al. |

FOREIGN PATENT DOCUMENTS

| | | |
|---|---|---|
| EP | 0 745 686 A1 | 12/1996 |
| EP | 0 258 017 B1 | 6/1997 |
| EP | 0 834 576 A2 | 4/1998 |
| WO | WO 90/13666 A1 | 11/1990 |
| WO | WO 91/13075 A2 | 9/1991 |
| WO | WO 93/21340 A1 | 10/1993 |
| WO | WO 95/06138 A1 | 3/1995 |
| WO | WO 96/27025 A1 | 9/1996 |
| WO | WO 98/44152 A1 | 10/1998 |
| WO | WO 99/05315 A2 | 2/1999 |
| WO | WO 99/19341 | 4/1999 |
| WO | WO 00/06770 A1 | 2/2000 |
| WO | WO 00/09757 A1 | 2/2000 |
| WO | WO 00/36151 A1 | 6/2000 |
| WO | WO 00/36152 A1 | 6/2000 |
| WO | WO 00/40750 A1 | 7/2000 |
| WO | WO 00/53805 A1 | 9/2000 |
| WO | WO 00/53812 A2 | 9/2000 |
| WO | WO 00/58507 A1 | 10/2000 |
| WO | WO 00/60072 A1 | 10/2000 |
| WO | WO 00/60114 A2 | 10/2000 |
| WO | WO 01/13088 A1 | 2/2001 |
| WO | WO 01/16375 A2 | 3/2001 |
| WO | WO 01/23610 A2 | 4/2001 |
| WO | WO 01/25480 A2 | 4/2001 |
| WO | WO 01/32930 A1 | 5/2001 |
| WO | WO 01/57248 A2 | 8/2001 |
| WO | WO 01/57249 A1 | 8/2001 |
| WO | WO 01/94609 A1 | 12/2001 |
| WO | WO 02/02813 A2 | 1/2002 |
| WO | WO 02/03305 A2 | 1/2002 |
| WO | WO 02/29106 A2 | 4/2002 |
| WO | WO 02/061126 A2 | 8/2002 |
| WO | WO 02/061127 A2 | 8/2002 |
| WO | WO 02/072892 A1 | 9/2002 |
| WO | WO 02/095070 A2 | 11/2002 |
| WO | WO 02/101095 A1 | 12/2002 |
| WO | WO 03/016565 A2 | 2/2003 |
| WO | WO 03/020734 A2 | 3/2003 |

OTHER PUBLICATIONS

Eggeling, et al. Monitoring Conformational Dynamics Of A Single Molecule By Selective Fluorescence Spectroscopy. *Proc. Natl. Acad. Sci. USA*. 1998; 95, 1556-1561.

Goodwin, et al. Application of Single Molecule Detection to DNA Sequencing. *Nucleosides & Nucleotides* 1997; 16:5 &6, 543-550.

Ronaghi, et al. A Sequencing Method Based on Real-Time Pyrophosphate. *Science* 1998; 281, 363-365.

Sanger, et al. DNA Sequencing With Chain-Terminating Inhibitors. *Proc. Natl. Acad. Sci USA* 1977; 74:12, 5463-5467.

Davis, L.M. et al., "Rapid DNA Sequencing Based Upon Single Molecule Detection" (1991) *Genetic Analysis Techniques and Applications*, 8(1):1-7.

Dobrikov, M.I., et al., "Sensitized Photomodification of Sinlge-Stranded DNA by a Binary System of Oligonucleotide Conjugates" (1997) *Antisense Nucleic Acid Drug Development*, 7(4):309-317.

Doore, K., et al., "Techniques for Single Molecule Sequencing " (1997) vol. 5: 139-152.

Harding, J.D., et al., "Single-Molecule Detection as an Approach to Rapid DNA Sequencing" (1992) *Trends in Biotechnol.*, 10(1-2): 57-57.

Kawata, Y., et al., "Feasibility of Molecular-Resolution Fluorescence Near-Field Microscopy Using Multi-Photon Absorption and Field Enhancement Near a Sharp Tip" (1999) *Journal of Applied Physics* 85(3): 1294-1301.

Kristensen, T., et al., "Rapid and Simple Preparation of Plasmids Suitable for Dideoxy DNA Sequencing and Other Purposes" (1991) *DNA Seq.* 1(4): 227-232.

Nickerson, D.A., et al., "PolyPhred: Automating the Detection and Genotyping of Single Nucleotide Substitutions Using Fluorescence-Based Resequencing" (1997) *Nucleic Acids Res.*, 25(14): 2745-2751.

Novotny, L. et al., "Theory of Nanometric Optical Tweezers" (1997) *Physical Review Letters* 79(4):645-648.

Sanchez, E.J., et al., "Near-Field Fluorescence Microscopy Based on Two-Photon Excitation with Metal Tips" (1999) *Phyiscal Review Letters* 82(20): 4014-4017.

Voss, H., et al., "Automated Cycle Sequencing with Taquenase: Protocols for Internal Labeling, Dye Primer and "Doublex" Simultaneous Sequencing" (1997) *BioTechniques*, 23(2): 312-318.

Schwille, P., et al., "Dual-Color Fluorescence Cross-Correlation Spectroscopy for Multicomponent Diffusional Analysis in Solution" (1997) *Biophysical Journal* 72:1878-86.

Weiss, S. "Fluorescence Spectroscopy of Single Biomolecules" (1999) *Science* 283: 1676-83.

* cited by examiner

Figure 10
A.
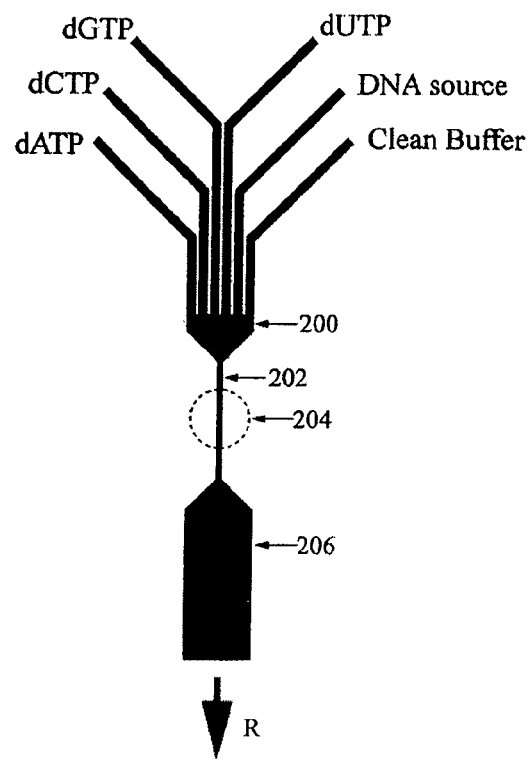
B.
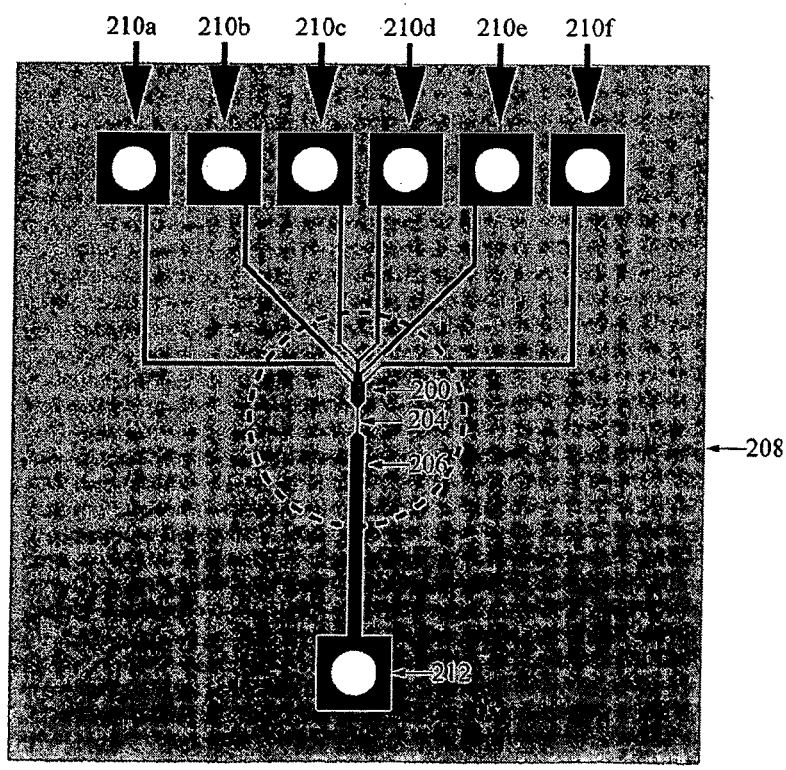

SEQUENCE LISTING

<160> NUMBER OF SEQ ID NOS: 2

<210> SEQ ID NO 1
<211> LENGTH: 6
<212> TYPE: DNA
<213> ORGANISM: Artificial
<220> FEATURE:
<223> OTHER INFORMATION: Oligonucleotide

<400> SEQUENCE: 1 atacta                                                                      6

<210> SEQ ID NO 2
<211> LENGTH: 6
<212> TYPE: DNA
<213> ORGANISM: Artificial
<220> FEATURE:
<223> OTHER INFORMATION: Oligonucleotide

<400> SEQUENCE: 2 tatgat                                                                      6

METHOD FOR SEQUENCING NUCLEIC ACID MOLECULES

CROSS REFERENCE TO RELATED APPLICATIONS

This application is a Continuation of U.S. patent application Ser. No. 09/572,530 filed on May 17, 2000, which claims the benefit of U.S. Provisional Patent Application Ser. No. 60/134,827, filed May 19, 1999, the entire disclosures of which are hereby incorporated herein by reference.

FIELD OF THE INVENTION

The present invention relates to a method for determining the sequence of nucleic acid molecules.

BACKGROUND OF THE INVENTION

The goal to elucidate the entire human genome has created an interest in technologies for rapid DNA sequencing, both for small and large scale applications. Important parameters are sequencing speed, length of sequence that can be read during a single sequencing run, and amount of nucleic acid template required. These research challenges suggest aiming to sequence the genetic information of single cells without prior amplification, and without the prior need to clone the genetic material into sequencing vectors. Large scale genome projects are currently too expensive to realistically be carried out for a large number of organisms or patients. Furthermore, as knowledge of the genetic basis for human diseases increases, there will be an ever-increasing need for accurate, high-throughput DNA sequencing that is affordable for clinical applications. Practical methods for determining the base pair sequences of single molecules of nucleic acids, preferably with high speed and long read lengths, would provide the necessary measurement capability.

Two traditional techniques for sequencing DNA are the dideoxy termination method of Sanger (Sanger et al., *Proc. Natl. Acad. Sci. U.S.A.* 74: 563–5467 (1977)) and the Maxam-Gilbert chemical degradation method (Maxam and Gilbert, *Proc. Natl. Acad. Sci. U.S.A.* 74: 560–564 (1977)). Both methods deliver four samples with each sample containing a family of DNA strands in which all strands terminate in the same nucleotide. Ultrathin slab gel electrophoresis, or more recently capillary array electrophoresis is used to resolve the different length strands and to determine the nucleotide sequence, either by differentially tagging the strands of each sample before electrophoresis to indicate the terminal nucleotide, or by running the samples in different lanes of the gel or in different capillaries. Both the Sanger and the Maxam-Gilbert methods are labor- and time-intensive, and require extensive pretreatment of the DNA source. Attempts have been made to use mass spectroscopy to replace the time-intensive electrophoresis step. For review of existing sequencing technologies, see Cheng "High-Speed DNA-Sequence Analysis," *Prog. Biochem. Biophys.* 22: 223–227 (1995).

Related methods using dyes or fluorescent labels associated with the terminal nucleotide have been developed, where sequence determination is also made by gel electrophoresis and automated fluorescent detectors. For example, the Sanger-extension method has recently been modified for use in an automated micro-sequencing system which requires only sub-microliter volumes of reagents and dye-labelled dideoxyribonucleotide triphosphates. In U.S. Pat. No. 5,846,727 to Soper et al., fluorescence detection is performed on-chip with one single-mode optical fiber carrying the excitation light to the capillary channel, and a second single-mode optical fiber collecting the fluorescent photons. Sequence reads are estimated in the range of 400–500 bases which is not a significant improvement over the amount of sequence information obtained with traditional Sanger or Maxam-Gilbert methods. Furthermore, the Soper method requires PCR amplification of template DNA, and purification and gel electrophoresis of the oligonucleotide sequencing 'ladders,' prior to initiation of the separation reaction. These systems all require significant quantities of target DNA. Even the method described in U.S. Pat. No. 5,302,509 to Cheeseman, which does not use gel electrophoresis for sequence determination, requires at least a million DNA molecules.

In a recent improvement of a sequencing-by-synthesis methodology originally devised ten years ago, DNA sequences are being deduced by measuring pyrophosphate release upon testing DNA/polymerase complexes with each deoxyribonucleotide triphosphate (dNTP) separately and sequentially. See Ronaghi et al., "A Sequencing Method Based on Real-Time Pyrophosphate," *Science* 281: 363–365 (1998) and Hyman, "A New Method of Sequencing DNA," *Anal. Biochem.* 174: 423–436 (1988). While using native nucleotides, the method requires synchronization of polymerases on the DNA strands which greatly restricts sequence read lengths. Only about 40 nucleotide reads were achieved, and it is not expected that the detection method can approach single molecule sensitivity due to limited quantum efficiency of light production by luciferase in the procedure presented by Ronaghi et al., "A Sequencing Method Based on Real-Time Pyrophosphate," *Science* 281: 363–365 (1998). Furthermore, the overall sequencing speed is limited by the necessary washing steps, subsequent chemical steps in order to identify pyrophosphate presence, and by the inherent time required to test each base pair to be sequenced with all the four bases sequentially. Also, difficulties in accurately determining homonucleotide stretches in the sequences were recognized.

Previous attempts for single molecule sequencing (generally unsuccessful but seminal) have utilized exonucleases to sequentially release individual fluorescently labelled bases as a second step after DNA polymerase has formed a complete complementary strand. See Goodwin et al., "Application of Single Molecule Detection to DNA Sequencing," *Nucleos. Nucleot.* 16: 543–550 (1997). It consists of synthesizing a DNA strand labelled with four different fluorescent dNTP analogs, subsequent degradation of the labelled strand by the action of an exonuclease, and detection of the individual released bases in a hydrodynamic flow detector. However, both polymerase and exonuclease have to show activity on a highly modified DNA strand, and the generation of a DNA strand substituted with four different fluorescent dNTP analogs has not yet been achieved. See Dapprich et al., "DNA Attachment to Optically Trapped Beads in Microstructures Monitored by Bead Displacement," *Bioimaging* 6: 25–32 (1998). Furthermore, little precise information is known about the relation between the degree of labeling of DNA and inhibition of exonuclease activity. See Dörre et al., "Techniques for Single Molecule Sequencing," *Bioimaging* 5: 139–152 (1997).

In a second approach utilizing exonucleases, native DNA is digested while it is being pulled through a thin liquid film in order to spatially separate the cleaved nucleotides. See Dapprich et al., "DNA Attachment to Optically Trapped Beads in Microstructures Monitored by Bead Displacement," *Bioimaging* 6: 25–32 (1998). They then diffuse a short distance before becoming immobilized on a surface for detection. However, most exonucleases exhibit sequence- and structure-dependent cleavage rates, resulting in difficulties in data analysis and matching sets from partial sequences. In addition, ways to identify the bases on the detection surface still have to be developed or improved.

Regardless of the detection system, methods which utilize exonucleases have not been developed into methods that meet today's demand for rapid, high-throughput sequencing. In addition, most exonucleases have relatively slow turnover rates, and the proposed methods require extensive pretreatment, labeling and subsequent immobilization of the template DNA on the bead in the flowing stream of fluid, all of which make a realization into a simple high-throughput system more complicated.

Other, more direct approaches to DNA sequencing have been attempted, such as determining the spatial sequence of fixed and stretched DNA molecules by scanned atomic probe microscopy. Problems encountered with using these methods consist in the narrow spacing of the bases in the DNA molecule (only 0.34 nm) and their small physico-chemical differences to be recognized by these methods. See Hansma et al., "Reproducible Imaging and Dissection of Plasmid DNA Under Liquid with the Atomic Force Microscope," *Science* 256: 1180–1184 (1992).

In a recent approach for microsequencing using polymerase, but not exonuclease, a set of identical single stranded DNA (ssDNA) molecules are linked to a substrate and the sequence is determined by repeating a series of reactions using fluorescently labelled dNTPs. U.S. Pat. No. 5,302,509 to Cheeseman. However, this method requires that each base is added with a fluorescent label and 3'-dNTP blocking groups. After the base is added and detected, the fluorescent label and the blocking group are removed, and, then, the next base is added to the polymer.

Thus, the current sequencing methods either require both polymerase and exonuclease activity to deduce the sequence or rely on polymerase alone with additional steps of adding and removing 3'-blocked dNTPs. The human genome project has intensified the demand for rapid, small- and large-scale DNA sequencing that will allow high throughput with minimal starting material. There also remains a need to provide a method for sequencing nucleic acid molecules that requires only polymerase activity, without the use of blocking substituents, resulting in greater simplicity, easier miniaturizability, and compatibility to parallel processing of a single-step technique.

The present invention is directed to meeting the needs and overcoming deficiencies in the art.

SUMMARY OF THE INVENTION

The present invention relates to a method of sequencing a target nucleic acid molecule having a plurality of nucleotide bases. This method involves providing a complex of a nucleic acid polymerizing enzyme and the target nucleic acid molecule oriented with respect to each other in a position suitable to add a nucleotide analog at an active site complementary to the target nucleic acid. A plurality of types of nucleotide analogs are provided proximate to the active site, wherein each type of nucleotide analog is complementary to a different nucleotide in the target nucleic acid sequence. A nucleotide analog is polymerized at an active site, wherein the nucleotide analog being added is complementary to the nucleotide of the target nucleic acid, leaving the added nucleotide analog ready for subsequent addition of nucleotide analogs. The nucleotide analog added at the active site as a result of the polymerizing step is identified. The steps of providing a plurality of nucleotide analogs, polymerizing, and identifying are repeated so that the sequence of the target nucleic acid is determined.

Another aspect of the present invention relates to an apparatus suitable for sequencing a target nucleic acid molecule. This apparatus includes a support as well as a nucleic acid polymerizing enzyme or oligonucleotide primer suitable to bind to a target nucleic acid molecule, where the polymerase or oligonucleotide primer is positioned on the support. A microstructure defines a confined region containing the support and the nucleic acid polymerizing enzyme or the oligonucleotide primer which is configured to permit labeled nucleotide analogs that are not positioned on the support to move rapidly through the confined region.

A further feature of the present invention involves an apparatus suitable for sequencing a target nucleic acid molecule. This apparatus includes a solid support and a nucleic acid polymerizing enzyme or oligonucleotide primer suitable to hybridize to a target nucleic acid molecule, where the nucleic acid polymerizing enzyme or oligonucleotide primer is positioned on the support. A housing defines a confined region containing the support and the nucleic acid polymerizing enzyme or the oligonucleotide primer. The housing is constructed to facilitate identification of labeled nucleotide analogs positioned on the support. Optical waveguides proximate to the confined region focus activating radiation on the confined region and collect radiation from the confined region.

Numerous advantages are achieved with the present invention. Sequencing can be carried out with small amounts of nucleic acid, with the capability of sequencing single nucleic acid template molecules which eliminates the need for amplification prior to initiation of sequencing. Long read lengths of sequence can be deduced in one run, eliminating the need for extensive computational methods to assemble a gap-free full length sequence of long template molecules (e.g., bacterial artificial chromosome (BAC) clones). For two operational modes of the present inventions, the read length of the sequence is limited by the length of template to be sequenced, or the processivity of the polymerase, respectively. By using the appropriate enzymatic systems, e.g. with accessory proteins to initiate the sequencing reaction at specific sites (e.g., origins of replication) on the double-stranded template nucleic acid, preparative steps necessary for conventional sequencing techniques, such as subcloning into sequencing vectors, can be eliminated.

In addition, the sequencing method of the present invention can be carried out using polymerase and no exonuclease. This results in greater simplicity, easier miniaturizability, and compatibility to parallel processing of a single-step technique.

In regard to the latter advantage, some polymerases exhibit higher processivity and catalytic speeds than exonucleases, with over 10,000 bases being added before dissociation of the enzyme for the case of T7 DNA polymerase (compared to 3,000 bases for λ exonuclease). In some cases, e.g., T7 DNA polymerase complexed with T7 helicase/primase, processivity values are even higher, ranging into several 100,000 s. The rates of DNA synthesis can be very high, measured in vivo of 1,000 bases/sec and in vitro of 750 bases/sec (in contrast to 12 bases/sec degraded by λ exonuclease in vitro). See Kelman et al., "Processivity of DNA Polymerases: Two Mechanisms, One Goal," *Structure* 6: 121–125 (1998); Carter et al., "The Role of Exonuclease and Beta Protein of Phage Lambda in Genetic Recombination. II. Substrate Specificity and the Mode of Action of Lambda Exonuclease," *J. Biol. Chem.* 246: 2502–2512 (1971); Tabor et al., "*Escherichia coli* Thioredoxin Confers Processivity on the DNA Polymerase Activity of the Gene 5 Protein of Bacteriophage T7," *J. Biol. Chem.* 262: 16212–16223 (1987); and Kovall et al., "Toroidal Structure of Lambda-Exonuclease" *Science* 277: 1824–1827 (1997), which are hereby incorporated by reference. An incorporation rate of 750 bases/sec is approximately 150 times faster than the sequencing speed of one of the fully automated ABI PRISM 3700 DNA sequencers by Perkin Elmer Corp., Foster City, Calif., proposed to be utilized in a shot-gun sequencing strategy for the human genome. See Venter et al., "Shotgun Sequencing of the Human Genome," *Science* 280: 1540–1542 (1998), which is hereby incorporated by reference.

The small size of the apparatus that can be used to carry out the sequencing method of the present invention is also highly advantageous. The confined region of the template/polymerase complex can be provided by the microstructure apparatus with the possibility of arrays enabling a highly parallel operational mode, with thousands of sequencing reactions carried out sequentially or simultaneously. This provides a fast and ultrasensitive tool for research application as well as in medical diagnostics.

BRIEF DESCRIPTION OF DRAWINGS

FIG. 3C shows the sequence generated by these steps.

FIGS. 10A–B show systems for supplying reagents to a nanofabricated confinement system in accordance with the present invention. In particular, FIG. 10A is a schematic drawing which shows how reagents are provided and passed through the system. FIG. 10B is similar but shows this system on a single chip with pads to connect the system to fluid reservoirs.

DETAILED DESCRIPTION OF THE INVENTION

Figure 1:
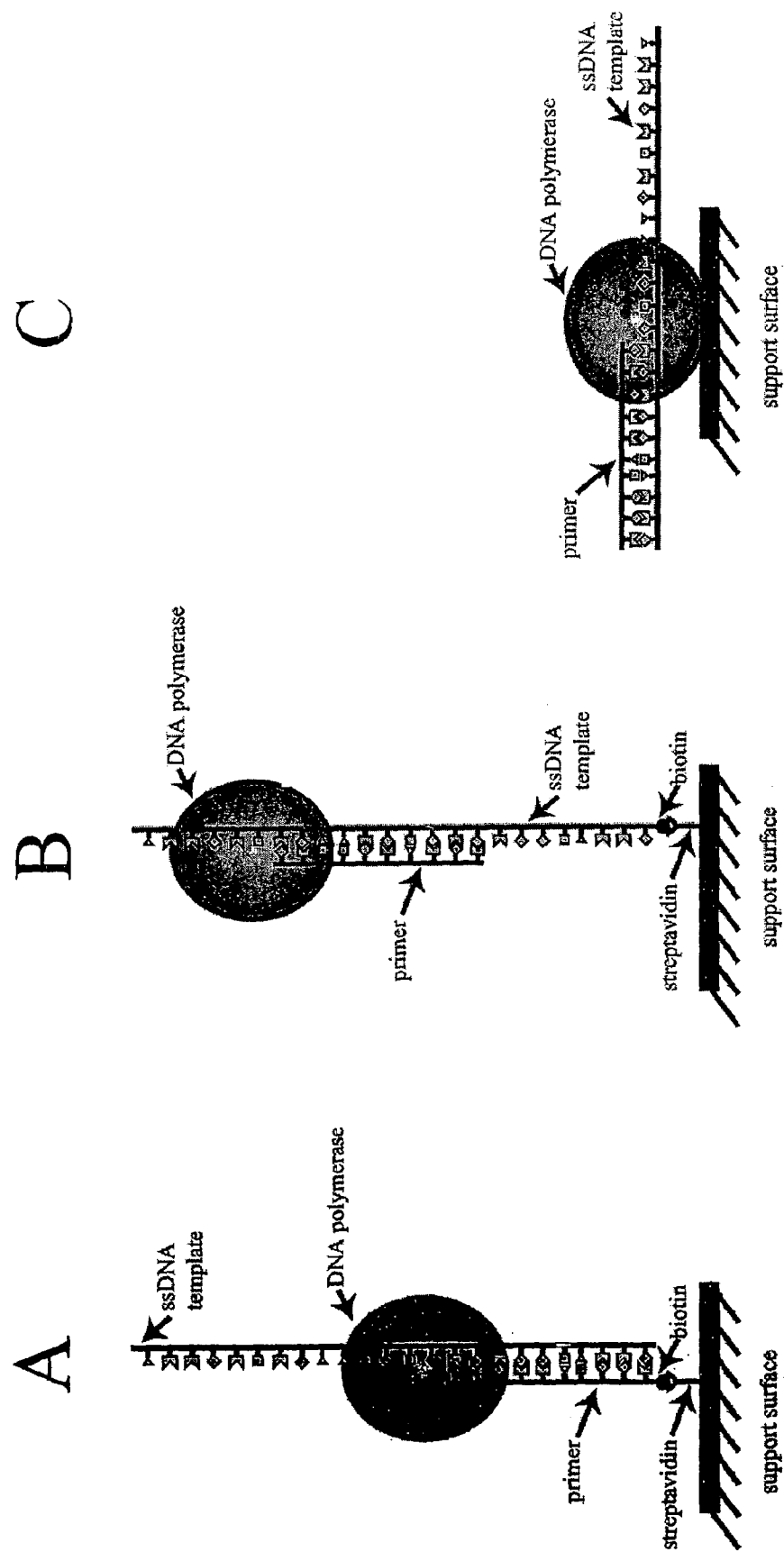
FIGS. 1A–C show 3 alternative embodiments for sequencing in accordance with the present invention.

The present invention relates to a method of sequencing a target nucleic acid molecule having a plurality of nucleotide bases. This method involves providing a complex of a nucleic acid polymerizing enzyme and the target nucleic acid molecule oriented with respect to each other in a position suitable to add a nucleotide analog at an active site complementary to the target nucleic acid. A plurality of types of nucleotide analogs are provided proximate to the active site, wherein each type of nucleotide analog is complementary to a different nucleotide in the target nucleic acid sequence. A nucleotide analog is polymerized at an active site, wherein the nucleotide analog being added is complementary to the nucleotide of the target nucleic acid, leaving the added nucleotide analog ready for subsequent addition of nucleotide analogs. The nucleotide analog added at the active site as a result of the polymerizing step is identified. The steps of providing a plurality of nucleotide analogs, polymerizing, and identifying are repeated so that the sequence of the target nucleic acid is determined.

Another aspect of the present invention relates to an apparatus suitable for sequencing a target nucleic acid molecule. This apparatus includes a support as well as a nucleic acid polymerizing enzyme or oligonucleotide primer suitable to bind to a target nucleic acid molecule, where the polymerase or oligonucleotide primer is positioned on the support. A microstructure defines a confined region containing the support and the nucleic acid polymerizing enzyme or the oligonucleotide primer which is configured to permit labeled nucleotide analogs that are not positioned on the support to move rapidly through the confined region.

A further feature of the present invention involves an apparatus suitable for sequencing a target nucleic acid molecule. This apparatus includes a support and a nucleic acid polymerizing enzyme or oligonucleotide primer suitable to hybridize to a target nucleic acid molecule, where the nucleic acid polymerizing enzyme or oligonucleotide primer is positioned on the support. A housing defines a confined region containing the support and the nucleic acid polymerizing enzyme or the oligonucleotide primer. The housing is constructed to facilitate identification of labeled nucleotide analogs positioned on the support. Optical waveguides proximate to the confined region focus activating radiation on the confined region and collect radiation from the confined region.

The present invention is directed to a method of sequencing a target nucleic acid molecule having a plurality of bases. In its fundamental principle, the temporal order of base additions during the polymerization reaction is measured on a single molecule of nucleic acid, i.e. the activity of a nucleic acid polymerizing enzyme, hereafter also referred to as polymerase, on the template nucleic acid molecule to be sequenced is followed in real time. The sequence is deduced by identifying which base is being incorporated into the growing complementary strand of the target nucleic acid by the catalytic activity of the nucleic acid polymerizing enzyme at each step in the sequence of base additions. In the preferred embodiment of the invention, recognition of the time sequence of base additions is achieved by detecting fluorescence from appropriately labelled nucleotide analogs as they are incorporated into the growing nucleic acid strand.

Accuracy of base pairing is provided by the specificity of the enzyme, with error rates of false base pairing of $10^{-5}$ or less. For enzyme fidelity, see Johnson, "Conformational Coupling in DNA-Polymerase Fidelity," *Ann. Rev. Biochem.* 62:685–713 (1993) and Kunkel, "DNA-Replication Fidelity," *J. Biol. Chem.* 267:18251–18254 (1992), which are hereby incorporated by reference.

The invention applies equally to sequencing all types of nucleic acids (DNA, RNA, DNA/RNA hybrids etc.) using a number of polymerizing enzymes (DNA polymerases, RNA polymerases, reverse transcriptases, mixtures, etc.). Therefore, appropriate nucleotide analogs serving as substrate molecules for the nucleic acid polymerizing enzyme can consist of members of the groups of dNTPs, NTPs, modified dNTPs or NTPs, peptide nucleotides, modified peptide nucleotides, or modified phosphate-sugar backbone nucleotides.

There are two convenient operational modes in accordance with the present invention. In the first operational mode of the invention, the template nucleic acid is attached to a support. This can be either by immobilization of (1) an oligonucleotide primer or (2) a single-stranded or (3) double-stranded target nucleic acid molecule. Then, either (1) the target nucleic acid molecule is hybridized to the attached oligonucleotide primer, (2) an oligonucleotide primer is hybridized to the immobilized target nucleic acid molecule, to form a primed target nucleic acid molecule complex, or (3) a recognition site for the polymerase is created on the double stranded template (e.g., through interaction with accessory proteins, such as a primase). A nucleic acid polymerizing enzyme on the primed target nucleic acid molecule complex is provided in a position suitable to move along the target nucleic acid molecule and extend the oligonucleotide primer at an active site. A plurality of labelled types of nucleotide analogs, which do not have a blocking substituent, are provided proximate to the active site, with each distinguishable type of nucleotide analog being complementary to a different nucleotide in the target nucleic acid sequence. The oligonucleotide primer is extended by using the nucleic acid polymerizing enzyme to add a nucleotide analog to the oligonucleotide primer at the active site, where the nucleotide analog being added is complementary to the nucleotide of the target nucleic acid at the active site. The nucleotide analog added to the oligonucleotide primer as a result of the extending step is identified. If necessary, the labeled nucleotide analog, which is added to the oligonucleotide primer, is treated before many further nucleotide analogs are incorporated into the oligonucleotide primer to insure that the nucleotide analog added to the oligonucleotide primer does not prevent detection of nucleotide analogs in subsequent polymerization and identifying steps. The steps of providing labelled nucleotide analogs, extending the oligonucleotide primer, identifying the added nucleotide analog, and treating the nucleotide analog are repeated so that the oligonucleotide primer is further extended and the sequence of the target nucleic acid is determined.

Alternatively, the above-described procedure can be carried out by first attaching the nucleic acid polymerizing enzyme to a support in a position suitable for the target nucleic acid molecule complex to move relative to the nucleic acid polymerizing enzyme so that the primed nucleic acid molecular complex is extended at an active site. In this embodiment, a plurality of labelled nucleotide analogs complementary to the nucleotide of the target nucleic acid at the active site are added as the primed target nucleic acid complex moves along the nucleic acid polymerizing enzyme. The steps of providing nucleotide analogs, extending the primer, identifying the added nucleotide analog, and treating the nucleotide analog during or after incorporation are repeated, as described above, so that the oligonucleotide primer is further extended and the sequence of the target nucleic acid is determined.

FIGS. 1A–C show 3 alternative embodiments for sequencing in accordance with the present invention. In FIG. 1A, a sequencing primer is attached to a support, e.g. by a biotin-streptavidin bond, with the primer hybridized to the target nucleic acid molecule and the nucleic acid polymerizing enzyme attached to the hybridized nucleic acid molecule at the active site where nucleotide analogs are being added to the sequencing primer. In FIG. 1B, the target nucleic acid molecule is attached to a support, with a sequencing primer hybridized to the template nucleic acid molecule and the nucleic acid polymerizing enzyme attached to the hybridized nucleic molecule at the active site where nucleotide analogs are being added to the sequencing primer. The primer can be added before or during the providing of nucleotide analogs. In addition to these scenarios, a double stranded target nucleic acid molecule can be attached to a support, with the target nucleic acid molecule harboring a recognition site for binding of the nucleic acid polymerizing enzyme at an active site where nucleotide analogs are being added to the primer. For example, such a recognition site can be established with the help of an accessory protein, such as an RNA polymerase or a helicase/primase, which will synthesize a short primer at specific sites on the target nucleic acid and thus provide a starting site for the nucleic acid polymerizing enzyme. See Richardson "Bacteriophage T7: Minimal Requirements for the Replication of a Duplex DNA Molecule," *Cell* 33: 315–317 (1983), which is hereby incorporated by reference. In FIG. 1C, the nucleic acid polymerizing enzyme is attached to a support, with the primed target nucleic acid molecule binding at the active site where nucleotide analogs are being added to the sequencing primer. As in the previous description, the nucleic acid polymerizing enzyme can likewise be attached to a support, but with the target nucleic acid molecule being double-stranded nucleic acid, harboring a recognition site for binding of the nucleic acid polymerizing enzyme at an active site where nucleotide analogs are being added to the growing nucleic acid strand. Although FIGS. 1A–C show only one sequencing reaction being carried out on the support, it is possible to conduct an array of several such reactions at different sites on a single support. In this alternative embodiment, each sequencing primer, target nucleic acid, or nucleic acid polymerizing enzyme to be immobilized on this solid support is spotted on that surface by microcontact printing or stamping, e.g., as is used for microarray technology of DNA chips, or by forming an array of binding sites by treating the surface of the solid support. It is also conceivable to combine the embodiments outlined in FIG. 1 and immobilize both the target nucleic acid molecule and the nucleic acid polymerizing enzyme proximate to each other.

The sequencing process of the present invention can be used to determine the sequence of any nucleic acid molecule, including double-stranded or single-stranded DNA, single stranded DNA hairpins, DNA/RNA hybrids, RNA with a recognition site for binding of the polymerase, or RNA hairpins.

The sequencing primer used in carrying out the process of the present invention can be a ribonucleotide, deoxyribonucleotide, modified ribonucleotide, modified deoxyribonucleotide, peptide nucleic acid, modified peptide nucleic acid modified phosphate-sugar backbone oligonucleotide, and other nucleotide and oligonucleotide analogs. It can be either synthetic or produced naturally by primases, RNA polymerases, or other oligonucleotide synthesizing enzymes.

The nucleic acid polymerizing enzyme utilized in accordance with the present invention can be either a thermostable polymerase or a thermally degradable polymerase. Examples for suitable thermostable polymerases include polymerases isolated from *Thermus aquaticus, Thermus thermophilus, Pyrococcus woesei, Pyrococcus furiosus, Thermococcus litoralis*, and *Thermotoga maritima*. Useful thermodegradable polymersases include *E. coli* DNA polymerase, the Klenow fragment of *E. coli* DNA polymerase, T4 DNA polymerase, T7 DNA polymerase, and others. Examples for other polymerizing enzymes that can be used to determine the sequence of nucleic acid molecules include *E. coli*, T7, T3, SP6 RNA polymerases and AMV, M-MLV and HIV reverse transcriptases. The polymerase can be bound to the primed target nucleic acid sequence at a primed single-stranded nucleic acid, an origin of replication, a nick or gap in a double-stranded nucleic acid, a secondary structure in a single-stranded nucleic acid, a binding site created by an accessory protein, or a primed single-stranded nucleic acid.

Materials which are useful in forming the support include glass, glass with surface modifications, silicon, metals, semiconductors, high refractive index dielectrics, crystals, gels, and polymers.

In the embodiments of FIG. 1, any suitable binding partner known to those skilled in the art could be used to immobilize either the sequencing primer, the target nucleic acid molecule, or the nucleic acid polymerizing enzyme to the support. Non-specific binding by adsorption is also possible. As shown in FIGS. 1A–C, a biotin-streptavidin linkage is suitable for binding the sequencing primer or the target nucleic acid molecule to the solid support. The biotin component of such a linkage can be attached to either the primer or nucleic acid or to the solid support with the streptavidin (or any other biotin-binding protein) being attached to the opposite entity.

One approach for carrying out this binding technique involves attaching PHOTOACTIVATABLE BIOTIN™ ("PAB") (Pierce Chemical Co., Rockford, Ill.) to a surface of the chamber used to carry out the sequencing procedure of the present invention. This can be achieved by exposure to light at 360 nm, preferably through a transparent wall of the chamber, as described in Hengsakul et al., "Protein Patterning with a Photoactivable Derivative of Biotin," *Bioconjugate Chem.* 7: 249–54 (1996), which is hereby incorporated by reference. When using a nanochamber, the biotin is activated in a diffraction-limited spot under an optical microscope. With near-field excitation, exposure can be self-aligned using a waveguide to direct light to the desired area. When exposed to light the PAB is activated and binds covalently to the interior surface of the channel. Excess unbound PAB is then removed by flushing with water.

Alternatively, streptavidin can be coated on the support surface. The appropriate nucleic acid primer oligonucleotide or the single stranded nucleic acid template is then biotinylated, creating an immobilized nucleic acid primer-target molecule complex by virtue of the streptavidin-biotin bound primer.

Another approach for carrying out the process of the present invention is to utilize complementary nucleic acids to link the sequencing primer or the target nucleic acid molecule to the solid support. This can be carried out by modifying a single stranded nucleic acid with a known leader sequence and ligating the known leader sequence to the sequencing primer or the target nucleic acid molecule. The resulting oligonucleotide may then be bound by hybridization to an oligonucleotide attached to the support and having a nucleotide sequence complementary to that of the known leader sequence. Alternatively, a second oligonucleotide can be hybridized to an end of the target nucleic acid molecule opposite to that bound to the oligonucleotide primer. That second oligonucleotide is available for hybridization to a complementary nucleic sequence attached to the support.

Reversible or irreversible binding between the support and either the oligonucleotide primer or the target nucleic acid sequence can be achieved with the components of any covalent or non-covalent binding pair. Other such approaches for immobilizing the sequencing primer or the target nucleic acid molecule to the support include an antibody-antigen binding pair and photoactivated coupling molecules.

In the embodiment of FIG. 1C, any technique known to be useful in reversibly or irreversibly immobilizing proteinaceous materials can be employed. It has been reported in the literature that RNA polymerase was successfully immobilized on activated surfaces without loss of catalytic activity. See Yin et al., "Transcription Against an Applied Force," *Science* 270:1653–1657 (1995), which is hereby incorporated by reference. Alternatively, the protein can be bound to an antibody, which does not interfere with its catalytic activity, as has been reported for HIV reverse transcriptase. See Lennerstrand et al., "A Method for Combined Immunoaffinity Purification and Assay of HIV-1 Reverse Transcriptase Activity Useful for Crude Samples," *Anal. Biochem.* 235:141–152 (1996), which is hereby incorporated by reference. Therefore, nucleic acid polymerizing enzymes can be immobilized without loss of function. The antibodies and other proteins can be patterned on inorganic surfaces. See James et al., "Patterned Protein Layers on Solid Substrates by Thin Stamp Microcontact Printing," *Langmuir* 14:741–744 (1998) and St John et al., "Diffraction-Based Cell Detection Using a Microcontact Printed Antibody Grating," *Anal. Chem.* 70:1108–1111 (1998), which are hereby incorporated by reference. Alternatively, the protein could be biotinylated (or labelled similarly with other binding molecules), and then bound to a streptavidin-coated support surface.

In any of the embodiments of FIGS. 1A to C, the binding partner and either the polymerase or nucleic acids they immobilize can be applied to the support by conventional chemical and photolithographic techniques which are well known in the art. Generally, these procedures can involve standard chemical surface modifications of the support, incubation of the support at different temperatures in different media, and possible subsequent steps of washing and incubation of the support surface with the respective molecules.

Alternative possibilities of positioning of the polymerizing complex are conceivable, such as by entrapment of the complex in a gel harboring pores too small to allow passage of the complex, but large enough to accommodate delivery of nucleotide analogs. Suitable media include agarose gels, polyacrylamide gels, synthetic porous materials, or nanostructures.

The sequencing procedure of the present invention can be initiated by addition of nucleic acid polymerizing enzyme to the reaction mixture in the embodiment of FIGS. 1A–B. For the embodiment of FIG. 1C, the primed nucleic acid can be added for initiation. Other scenarios for initiation can be employed, such as establishing a preformed nucleic acid-polymerase complex in the absence of divalent metal ions which are integral parts of the active sites of polymerases (most commonly $Mg^{2+}$). The sequencing reaction can then be started by adding these metal ions. The preinitiation complex of template could also be formed with the enzyme in the absence of nucleotides, with fluorescent nucleotide analogs being added to start the reaction. See Huber et al., "*Escherichia coli* Thioredoxin Stabilizes Complexes of Bacteriophage T7 DNA Polymerase and Primed Templates," *J. Biol. Chem.* 262:16224–16232 (1987), which is hereby incorporated by reference. Alternatively, the process can be started by uncaging of a group on the oligonucleotide primer which protects it from binding to the nucleic acid polymerizing enzyme. Laser beam illumination would then start the reaction coincidentally with the starting point of observation.

Figure 2:
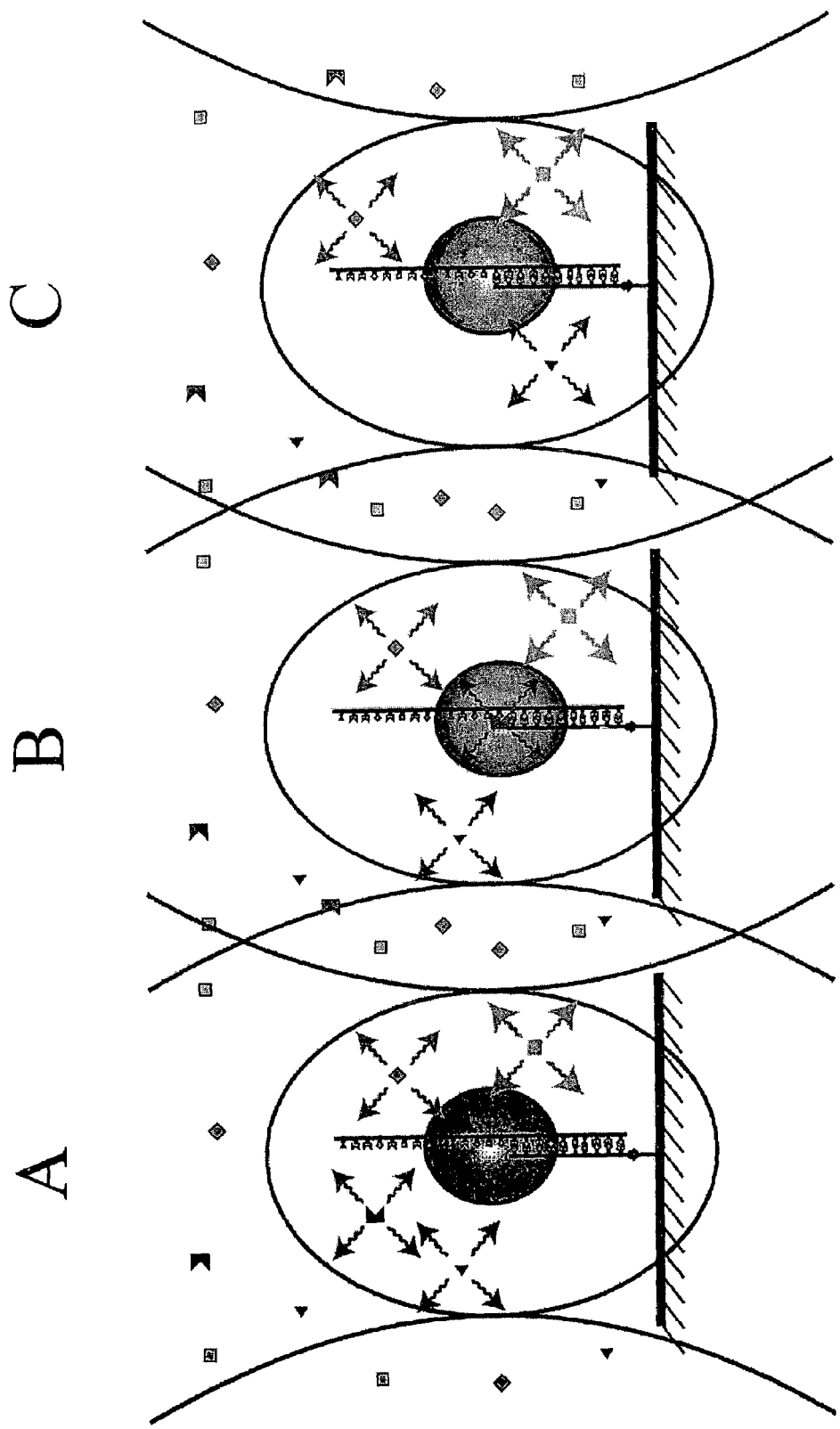
FIGS. 2A–C are schematic drawings showing the succession of steps used to sequence nucleic acids in accordance with the present invention.

FIGS. 2A–C are schematic drawings showing the succession of steps used to sequence nucleic acids in accordance with the present invention.

In FIG. 2A, labelled nucleotide analogs are present in the proximity of the primed complex of a nucleic acid polymerizing enzyme attached to the hybridized sequencing primer and target nucleic acid molecule which are attached on the solid support. During this phase of the sequencing process, the labelled nucleotide analogs diffuse or are forced to flow through the extension medium towards and around the primed complex.

In accordance with FIG. 2B, once a nucleotide analog has reached the active site of the primed complex, it is bound to it and the nucleic acid polymerizing enzyme establishes whether this nucleotide analog is complementary to the first open base of the target nucleic acid molecule or whether it represents a mismatch. The mismatched base will be rejected with the high probability that corresponds to the above-mentioned high fidelity of the enzyme, whereas the complementary nucleotide analog is polymerized to the sequencing primer to extend the sequencing primer.

During or after each labelled nucleotide analog is added to the sequencing primer, the nucleotide analog added to the sequencing primer is identified. This is most efficiently achieved by giving each nucleotide analog a different distinguishable label. By detecting which of the different labels are added to the sequencing primer, the corresponding nucleotide analog added to the sequencing primer can be identified and, by virtue of its complementary nature, the base of the target nucleic acid which the nucleotide analog complements can be determined. Once this is achieved, it is no longer necessary for the nucleotide analog that was added to the sequencing primer to retain its label. In fact, the continued presence of labels on nucleotide analogs complementing bases in the target nucleic acid that have already been sequenced would very likely interfere with the detection of nucleotide analogs subsequently added to the primer. Accordingly, labels added to the sequencing primer are removed after they have been detected, as shown in FIG. 2C. This preferably takes place before additional nucleotide analogs are incorporated into the oligonucleotide primer.

By repeating the sequence of steps described in FIGS. 2A–C, the sequencing primer is extended and, as a result, the entire sequence of the target nucleic acid can be determined. Although the immobilization embodiment depicted in FIGS. 2A–C is that shown in FIG. 1A, the alternative immobilization embodiments shown in FIGS. 1B–C could similarly be utilized in carrying out the succession of steps shown in FIGS. 2A–C.

In carrying out the diffusion, incorporation, and removal steps of FIGS. 2A–C, an extension medium containing the appropriate components to permit the nucleotide analogs to be added to the sequencing primer is used. Suitable extension media include, e.g., a solution containing 50 mM Tris-HCl, pH 8.0, 25 mM $MgCl_2$, 65 mM NaCl, 3 mM DTT, (this is the extension medium composition recommended by the manufacturer for Sequenase, a T7 mutant DNA polymerase), and nucleotide analogs at an appropriate concentration to permit the identification of the sequence. Other media that are appropriate for this and other polymerases are possible, with or without accessory proteins, such as single-stranded binding proteins. Preferably, the extension phase is carried out at 37° C. for most thermally degradable polymerases, although other temperatures at which the polymerase is active can be employed.

Once a labelled nucleotide analog is added to the sequencing primer, as noted above, the particular label of the added moiety must be identified in order to determine which type of nucleotide analog was added to the sequencing primer and, as a result, what the complementary base of target nucleic acid is. How the label of the added entity is determined depends upon the type of label being utilized. For the preferred embodiment of the invention, discussion of the identification steps will be restricted to the employment of nucleotide analogs carrying fluorescent moieties. However, other suitable labels include chromophores, enzymes, antigens, heavy metals, magnetic probes, dyes, phosphorescent groups, radioactive materials, chemiluminescent moieties, scattering or fluorescent nanoparticles, Raman signal generating moieties, and electrochemical detecting moieties. Such labels are known in the art and are disclosed for example in Prober, et. al., *Science* 238: 336–41 (1997); Connell et. al., *BioTechniques* 5(4): 342–84 (1987); Ansorge, et. al., *Nucleic Acids Res.* 15(11): 4593–602 (1987); and Smith et. al., *Nature* 321:674 (1986), which are hereby incorporated by reference. In some cases, such as for chromophores, fluorophores, phosphorescent labels, nanoparticles, or Raman signaling groups, it is necessary to subject the reaction site to activating radiation in order to detect the label. This procedure will be discussed in detail below for the case of fluorescent labels. Suitable techniques for detecting the fluorescent label include time-resolved far-field microspectroscopy, near-field microspectroscopy, measurement of fluorescence resonance energy transfer, photoconversion, and measurement of fluorescence lifetimes. Fluorophore identification can be achieved by spectral wavelength discrimination, measurement and separation of fluorescence lifetimes, fluorophore identification, and/or background suppression. Fluorophore identification and/or background suppression can be facilitated by fast switching between excitation modes and illumination sources, and combinations thereof.

FIGS. 3A–B show plots of fluorescence signals vs. time during the succession of steps (outlined in FIG. 2) that is used to carry out the sequencing procedure of the present invention. In essence, in this procedure, an incorporated nucleotide analog will be distinguished from unincorporated ones (randomly diffusing through the volume of observation or being convected through it by hydrodynamic or electrophoretic flow) by analyzing the time trace of fluorescence for each distinguishable label simultaneously. This is achieved by photon burst recordings and time-resolved fluorescence correlation spectroscopy which distinguishes the continuing steady fluorescence of the incorporated label (until removed by the mechanisms discussed below) from the intermittent emission of the free fluorophores. See Magde et al., "Thermodynamic Fluctuations in a Reacting System—Measurement by Fluorescence Correlation Spectroscopy," *Phys. Rev. Lett.* 29:705–708 (1972), Kask P. et al., "Fluorescence-Intensity Distribution Analysis and its Application in Biomolecular Detection Technology," *Proc. Nat. Acad. Sci. U.S.A.* 96: 13756–13761 (1999), and Eggeling et al., "Monitoring Conformational Dynamics of a Single Molecule by Selective Fluorescence Spectroscopy," *Proc. Nat. Acad. Sci. U.S.A.* 95: 1556–1561 (1998), which are hereby incorporated by reference. The sequence can be deduced by combining time traces of all detection channels.

FIG. 3A shows a plot of fluorescence signal vs. time during just the diffusion phase of FIG. 2A, assuming four different channels of fluorescence detection for the four different bases (e.g., by employing four different labels, each with a different fluorescence emission spectrum, by which they can be separated through optical filters). Each peak in FIG. 3A represents the burst of fluorescence resulting from the presence of a nucleotide analog in the volume of observation, with each different nucleotide analog being distinguished by its different label which generates peaks of different colors (depicted in FIG. 3A by different line patterns). The narrow width of these peaks indicates that the nucleotide analogs have a brief residence time proximate to the active site of sequencing, because they are freely diffusing or flowing through the volume of observation. A peak of similar width is expected for the case of a mismatched nucleotide analog transiently binding to the active site of the nucleic acid polymerizing enzyme, and subsequent rejection of incorporation by the enzyme.

FIG. 3B shows a plot of fluorescence signal vs. time during the incorporation and subsequent removal phases of FIGS. 2B–C. As in FIG. 3A, each peak of FIG. 3B represents the presence of a nucleotide analog with each different nucleotide analog being distinguished by its different label which generates peaks of different colors (depicted in FIG. 3B by different line patterns). The narrow width of some peaks in FIG. 3B again relates to the nucleotide analogs which remain mobile within the extension medium and do not extend the sequencing primer. Such narrow peaks result because these nucleotide analogs have a brief residence time proximate to the active site of sequencing, as explained for FIG. 3A. On the other hand, the wider peaks correspond to nucleotide analogs which have, at the active site, complementary bases on the template nucleic acid molecule and serve to extend the sequencing primer. As a result of their immobilization, these nucleotide analogs have wider peaks, because they will remain in the observation volume during and after incorporation in the growing nucleic acid strand, and thus continue to emit fluorescence. Their signal is only terminated later in time as a result of the subsequent removal step which eliminates continued fluorescence, and allowing the identification of subsequent incorporation events.

Moving from left to right in FIG. 3B (i.e. later in time), the sequence of wider peaks corresponds to the complement of the sequence of the template nucleic acid molecule. FIG. 3C shows the final output of FIG. 3B which can be achieved, for example, by a computer program that detects the short bursts of fluorescence and discards them in the final output. As a result of such filtering, only the peaks generated by immobilized nucleotide analogs are present, and converted into the sequence corresponding to the complement of sequence of the template nucleic acid molecule. This complementary sequence is here ATACTA, therefore, the order of the bases of the template nucleic acid molecule being sequenced is TATGAT.

Fluorescent labels can be attached to nucleotides at a variety of locations. Attachment can be made either with or without a bridging linker to the nucleotide. Conventionally used nucleotide analogs for labeling of nucleic acid with fluorophores carry the fluorescent moiety attached to the base of the nucleotide substrate molecule. However, it can also be attached to a sugar moiety (e.g., deoxyribose) or the alpha phosphate. Attachment to the alpha phosphate might prove advantageous, because this kind of linkage leaves the internal structure of the nucleic acid intact, whereas fluorophores attached to the base have been observed to distort the double helix of the synthesized molecule and subsequently inhibit further polymerase activity. See Zhu et al., "Directly Labelled DNA Probes Using Fluorescent Nucleotides with Different Length Linkers," *Nucleic Acids Res.* 22: 3418–3422 (1994), and Doublie et al., "Crystal Structure of a Bacteriophage T7 DNA Replication Complex at 2.2 Ångstrom Resolution," *Nature* 391:251–258 (1998), which are hereby incorporated by reference. Thus, thiol-group-containing nucleotides, which have been used (in the form of NTPs) for cross-linking studies on RNA polymerase, could serve as primary backbone molecules for the attachment of suitable linkers and fluorescent labels. See Hanna et al., "Synthesis and Characterization of a New Photo-Cross-Linking CTP Analog and Its Use in Photoaffinity-Labeling *Escherichia-coli* and T7-RNA Polymerases," *Nucleic Acids Res.* 21:2073–2079 (1993), which is hereby incorporated by reference.

In the conventional case where the fluorophore is attached to the base of the nucleotide, it is typically equipped with fluorophores of a relatively large size, such as fluorescein. However, smaller fluorophores, e.g., pyrene or dyes from the coumarin family, could prove advantageous in terms of being tolerated to a larger extent by polymerases. In fact, it is possible to synthesize a DNA fragment of 7,300 base pair length in which one base type is fully replaced by the corresponding coumarin-labelled dNTP using T7 DNA polymerase, whereas the enzyme is not able to carry out the corresponding synthesis using fluorescein-labelled dNTPs.

In all of these cases, the fluorophore remains attached to the part of the substrate molecule that is incorporated into the growing nucleic acid molecule during synthesis. Suitable means for removal of the fluorophore after it has been detected and identified in accordance with the sequencing scheme of the present invention include photobleaching of the fluorophore or photochemical cleavage of the nucleotide and the fluorophore, e.g., cleavage of a chemical bond in the linker. Removal of the fluorescent label of already incorporated nucleotides, the rate of which can be adjusted by the laser power, prevents accumulation of signal on the nucleic acid strand, thereby maximizing the signal to background ratio for nucleotide identification. For this scheme, the objective of the present invention is to detect all of the photons from each label and then photobleach or photochemically cleave before or soon after the next few nucleotide is incorporated in order to maintain adequate signal to noise values for subsequent identification steps. The removal phase of the process of the present invention can be carried out by any procedure suitable for removing a label without damaging the sequencing reaction complex.

Figure 3:
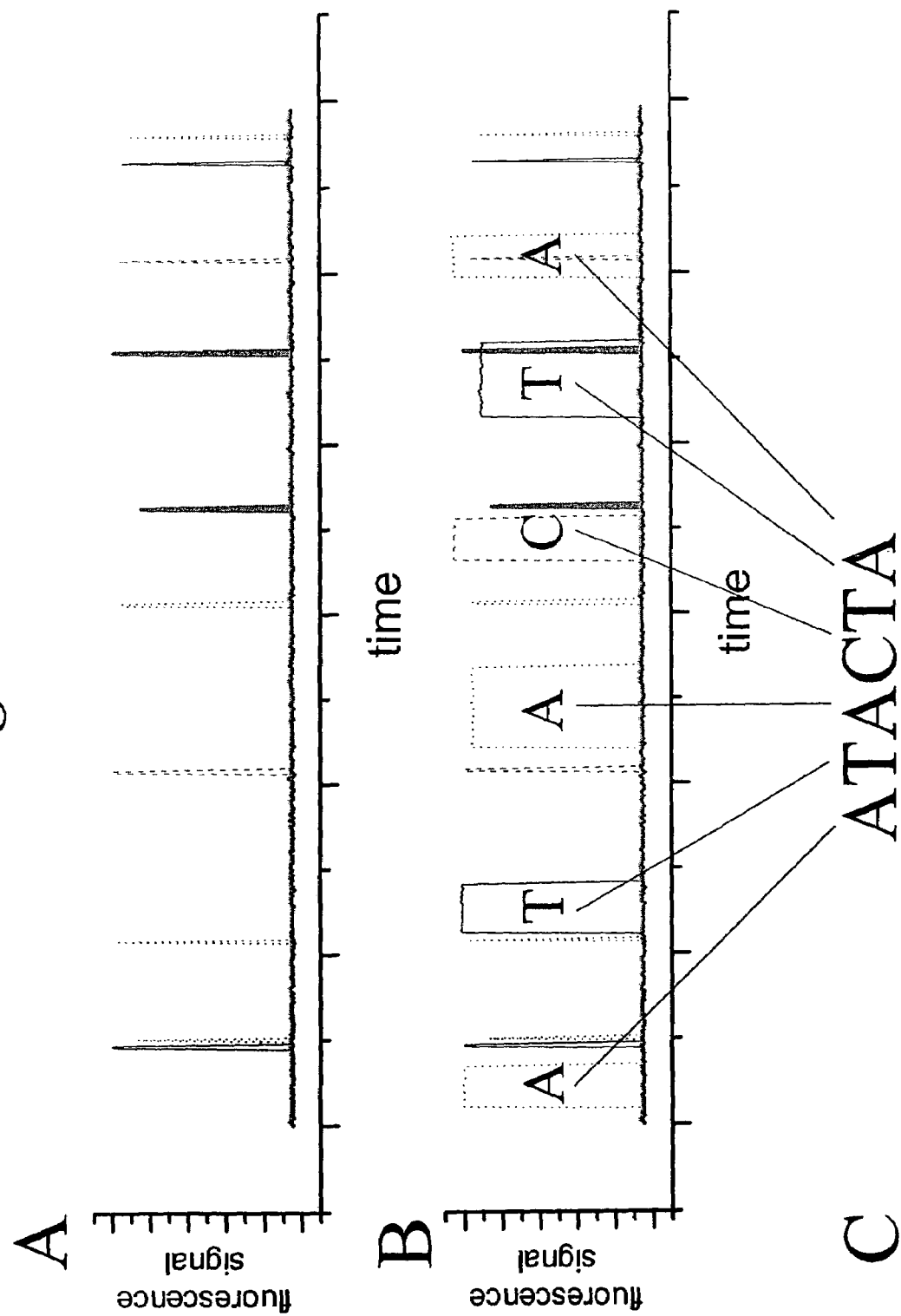
FIGS. 3A–C show plots of fluorescence signals vs. time during the succession of steps used to sequence the nucleic acid in accordance with the present invention.
Figure 4:
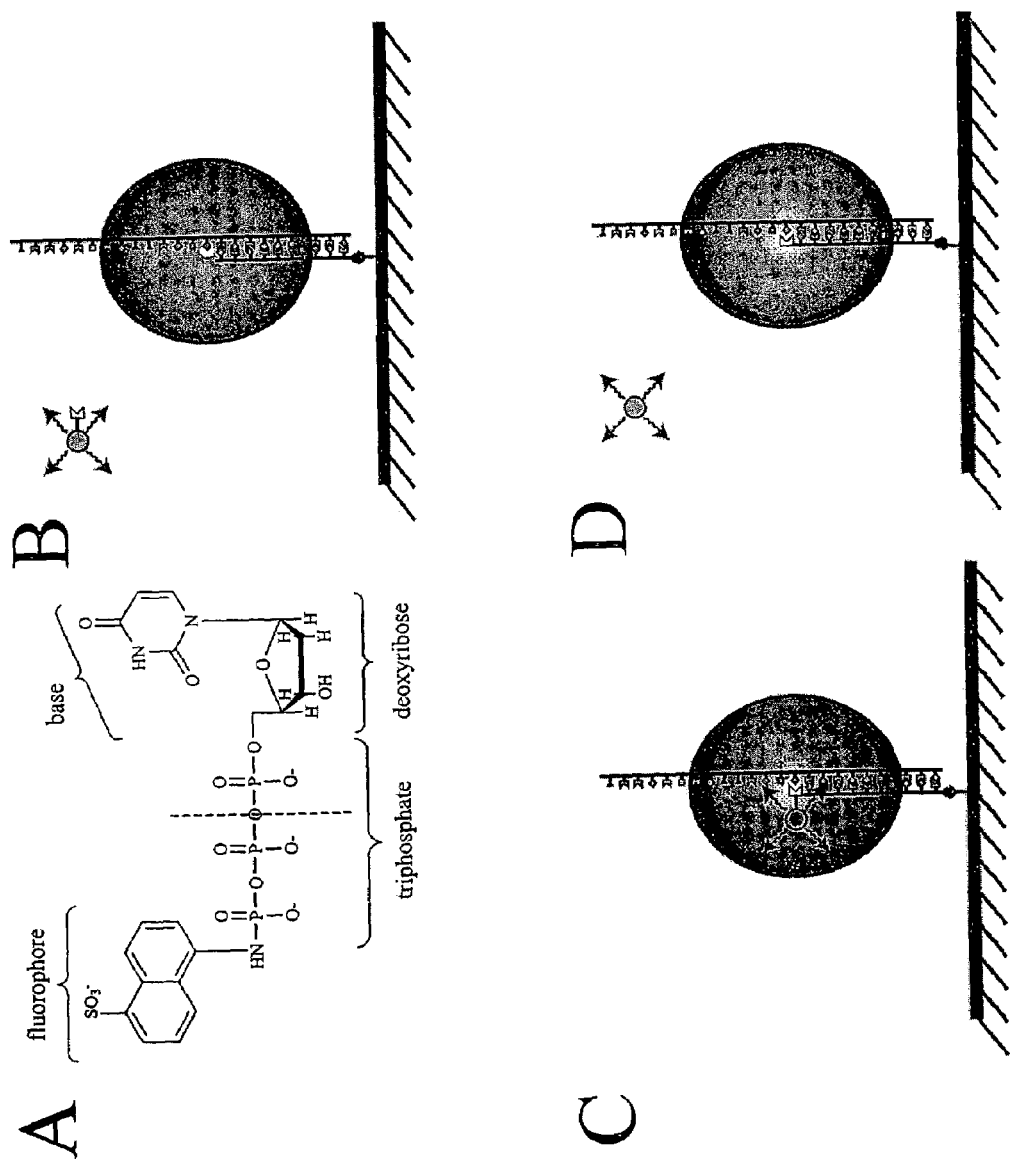
FIGS. 4A–D depict the structure and schematic drawings showing the succession of steps used to sequence the nucleic acid in accordance with the present invention in the case where fluorescent nucleotides carrying the label at the gamma phosphate position (here shown as a gamma-linked dNTP) are used.

In addition to fluorescent labels that remain in the nucleic acid during synthesis, nucleotides that are labelled fluorescently or otherwise and carry the label attached to either the beta or gamma phosphate of the nucleotide can also be used in the sequencing procedure of the present invention. Analogous compounds have previously been synthesized in the form of NTP analogs and have been shown to be excellent substrates for a variety of enzymes, including RNA polymerases. See Yarbrough et al., "Synthesis and Properties of Fluorescent Nucleotide Substrates for DNA-dependent RNA Polymerase," *Journal of Biological Chemistry* 254:12069–12073 (1979), and Chatterji et al., "Fluorescence Spectroscopy Analysis of Active and Regulatory Sites of RNA Polymerase," *Methods in Enzymology* 274: 456–479 (1996), which are hereby incorporated by reference. During the synthesis of DNA, the bond cleavage in the nucleotide occurs between the alpha and the beta phosphate, causing the beta and gamma phosphates to be released from the active site after polymerization, and the formed pyrophosphate subsequently diffuses or is convected away from the nucleic acid. In accordance with the present invention, it is possible to distinguish the event of binding of a nucleotide and its incorporation into nucleic acid from events just involving the binding (and subsequent rejection) of a mismatched nucleotide, because the rate constants of these two events are drastically different. The rate-limiting step in the successive elementary steps of DNA polymerization is a conformational change of the polymerase that can only occur after the enzyme has established that the correct (matched) nucleotide is bound to the active site. Therefore, an event of a mismatched binding of a nucleotide analog will be much shorter in time than the event of incorporation of the correct base. See Patel et al., "Pre-Steady-State Kinetic Analysis of Processive DNA Replication Including Complete Characterization of an Exonuclease-Deficient Mutant," *Biochemistry* 30: 511–525 (1991) and Wong et al., "An Induced-Fit Kinetic Mechanism for DNA Replication Fidelity: Direct Measurement by Single-Turnover Kinetics," *Biochemistry* 30: 511–525 (1991), which are hereby incorporated by reference. As a result, the fluorescence of the label that is attached to the beta or gamma phosphate of the nucleotide analog remains proximate to the polymerase for a longer time in case the nucleotide analog is polymerized, and can be distinguished in accordance to the scheme described above for FIG. 3. After incorporation, the label will diffuse away with the cleaved pyrophosphate. This procedure is shown in FIG. 4. FIG. 4A shows the structure of 1-aminonaphthalene-5-sulfonate (AmNS)-dUTP, a representative example of a nucleotide analog carrying a fluorescent label attached to the gamma phosphate, with the cleavage position indicated by the dashed line. FIG. 4B-D show the successive steps of incorporation and release of the pyrophosphate-fluorophore complex, in analogy to FIG. 2. The time trace of fluorescence for this scheme will be the same as shown in FIG. 3. Thus, this is an alternative scheme to the one outlined above in which the fluorophore is first incorporated into the nucleic acid and the signal is subsequently eliminated by photobleaching or photochemical cleavage after identification of the label.

The identification of the particular fluorescently labelled nucleotide analog that is incorporated against the background of unincorporated nucleotides diffusing or flowing proximally to the nucleic acid polymerizing enzyme can be further enhanced by employing the observation that for certain fluorescently labelled dNTPs (e.g., coumarin-5-dGTP, or AmNS-UTP), the presence of the base in the form of a covalent linkage significantly reduces (i.e. quenches) the fluorescence of the label. See Dhar et al., "Synthesis and Characterization of Stacked and Quenched Uridine Nucleotide Fluorophores," *Journal of Biological Chemistry* 274: 14568–14572 (1999), and Draganescu et al., "Fhit-Nucleotide Specificity Probed with Novel Fluorescent and Fluorogenic Substrates," *Journal of Biological Chemistry* 275: 4555–4560 (2000), which are hereby incorporated by reference. The interaction between the fluorophore and the base quenches the fluorescence, so that the molecule is not very fluorescent in solution by itself. However, when such a fluorescent nucleotide is incorporated into the nucleic acid, the fluorophore gets disconnected from the nucleotide and the fluorescence is no longer quenched. For the case of a linkage to the beta or gamma phosphate of the nucleotide, this occurs naturally through the enzymatic activity of the polymerase, in the case of fluorophores linked to the base, this would have to be accomplished by photochemical cleavage. The signal of fluorescence from the cleaved fluorophore is much brighter and can be detected over the possible background of the plurality of quenched molecules in the vicinity of the polymerase/nucleic acid complex.

Figure 5:
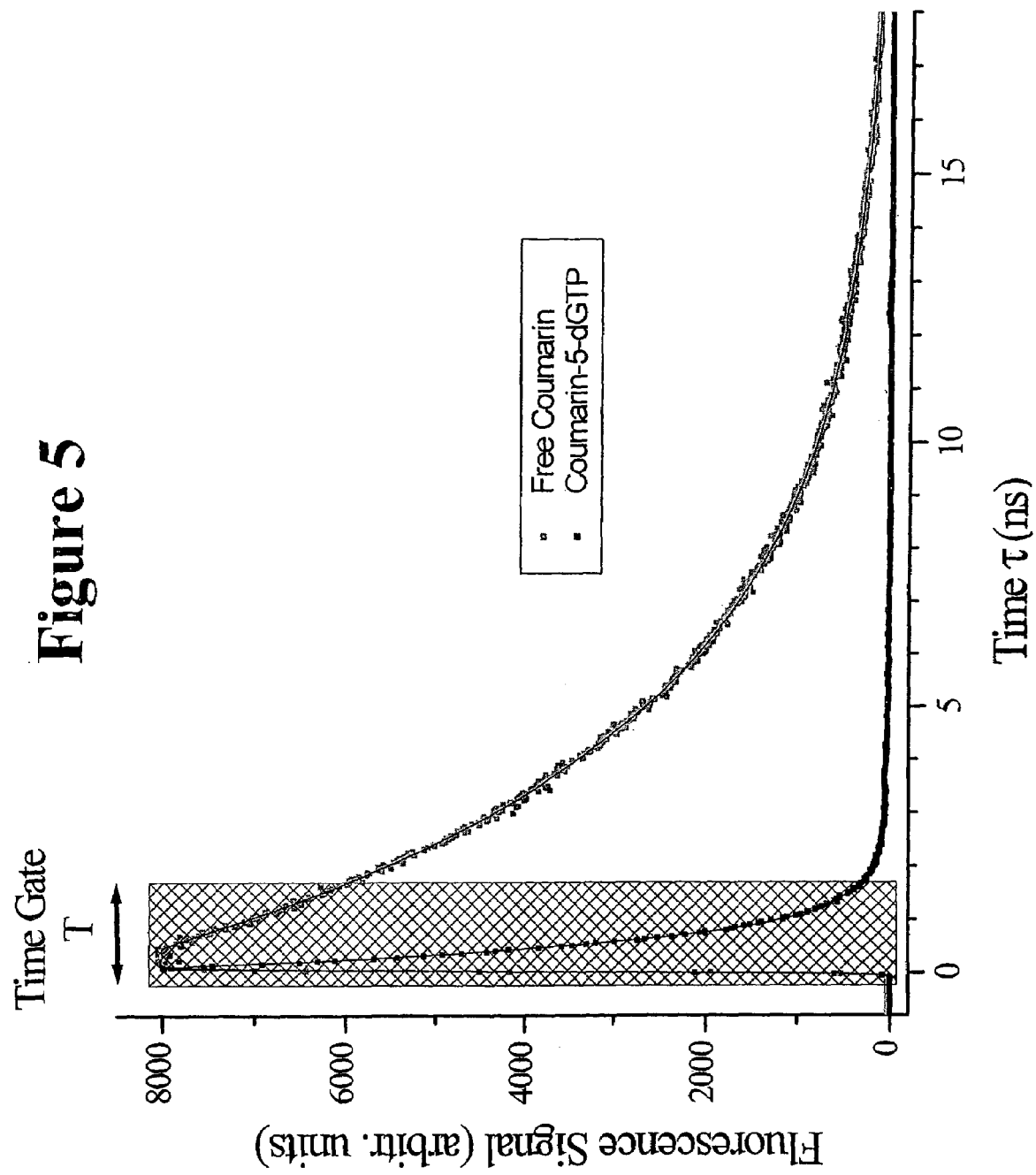
FIG. 5 shows the principle of discrimination of fluorophores by time-gated fluorescence decay time measurements, which can be used to suppress background signal in accordance with the present invention.

Furthermore, since the fluorescence lifetime of the quenched molecules diffusing in the solution is much shorter than the lifetime of the cleaved molecule, a further enhancement of signal to background can be achieved by employing pulsed illumination and time-gated photon detection. This is illustrated in FIG. 5, showing the time-resolved fluorescence decay curves for coumarin alone and coumarin-dGTP, respectively. Because the coumarin fluorescence is quenched upon covalent linkage to dGTP, the lifetime is much shorter than for the free dye alone, meaning that on average, fluorescent photons are emitted much sooner after an excitation pulse, e.g., delivered by a pulsed laser. By eliminating this time interval immediately after the pulse from detection, which can be achieved, for example, with a variable delay line component (indicated by the cross-hatched bar with adjustable delay time of width T), the response window of the detector can be gated such that only fluorescence emitted from the slow decay component, in this case the free dye (or, in terms of the sequencing scheme, the cleaved fluorophore) is detected, and thus background from unincorporated molecules is reduced even further. Saavedra et al. "Time-Resolved Fluorimetric Detection of Terbium-Labelled Deoxyribonucleic Acid Separated by Gel Electrophoresis," *Analyst* 114:835–838 (1989), which is hereby incorporated by reference.

Nucleotides can also be converted into fluorophores by photochemical reactions involving radical formation. This technique has been utilized with serotonin and other biologically relevant molecules. See Shear et al., "Multiphoton-Excited Visible Emission by Serotonin Solutions," *Photochem. Photobiol.* 65:931–936 (1997), which is hereby incorporated by reference. The ideal photophysical situation would be to have each nucleotide generate its own fluorescence signal. Unfortunately, nucleic acid and the individual nucleotides are poor fluorophores emitting weakly with minuscule quantum efficiencies and only on illumination with deep ultraviolet light. However, the native ultraviolet fluorophore serotonin (5HT) can be photoionized by simultaneous absorption of 4 infrared photons, to form a radical that reacts with other ground state molecules to form a complex that emits bright green fluorescence on absorption of 2 more photons. Subsequent discoveries showed that many small organic molecules can undergo this multiphoton conversion.

Known quenching of fluorophores by nucleic acid components and by neighboring fluorophores as well as resonance energy transfer may provide markers tolerated by the polymerase. Furey et al., "Use of Fluorescence Resonance Energy Transfer to Investigate the Conformation of DNA Substrates Bound to the Klenow Fragment," *Biochemistry*

37:2979–2990 (1998) and Glazer et al., "Energy-Transfer Fluorescent Reagents for DNA Analyses," *Curr. Op. Biotechn.* 8:94–102 (1997), which are hereby incorporated by reference.

In the most efficient setup of the present invention, each base should be distinguished by its own label so that the sequence can be deduced from the combined output of four different channels as illustrated in FIG. 3C. This can, for example, be accomplished by using different fluorophores as labels and four different detection channels, separated by optical filters. It is also possible to distinguish the labels by parameters other than the emission wavelength band, such as fluorescence lifetime, or any combination of several parameters for the different bases. Due to the possible interactions of a fluorophore with a base, it is feasible to employ the same fluorophore to distinguish more than one base. As an example, coumarin-dGTP has a much shorter fluorescence lifetime than coumarin-dCTP so that the two bases could be distinguished by their difference in fluorescence lifetime in the identification step of the sequencing scheme, although they carry the same chemical substance as the fluorescent label.

The sequencing procedure can also be accomplished using less than 4 labels employed. With 3 labels, the sequence can be deduced from sequencing a nucleic acid strand (1) if the $4^{th}$ base can be detected as a constant dark time delay between the signals of the other labels, or (2) unequivocally by sequencing both nucleic acid strands, because in this case one obtains a positive fluorescence signal from each base pair. Another possible scheme that utilizes two labels is to have one base labelled with one fluorophore and the other three bases with another fluorophore. In this case, the other 3 bases do not give a sequence, but merely a number of bases that occur between the particular base being identified by the other fluorophore. By cycling this identifying fluorophore through the different bases in different sequencing reactions, the entire sequence can be deduced from sequential sequencing runs. Extending this scheme of utilizing two labels only, it is even possible to obtain the full sequence by employing only two labelled bases per sequencing run. As was pointed out by Sauer et al., "Detection and Identification of Single Dye Labelled Mononucleotide Molecules Released From an Optical Fiber in a Microcapillary: First Steps Towards a New Single Molecule DNA Sequencing Technique," *Phys. Chem. Chem. Phys.* 1:2471–77 (1999), which is hereby incorporated by reference, the sequence can be determined with 2 labels alone if one carries out multiple sequencing reactions with the possible combinations of the two labels. Therefore, in carrying out the process of the present invention, it is desirable to label long stretches of nucleic acid with at least 2 different labels.

Where sequencing is carried out by attaching the polymerase rather than the nucleic acid to the support, it is important that the enzyme synthesizes long stretches of nucleic acid, without the nucleic acid/protein complex falling apart. This is called processive nucleic acid synthesis. At least for the system using T7 DNA polymerase and dCTP completely replaced by coumarin-5-dCTP, the synthesis is fully processive over at least 7300 basepairs (i.e., one polymerase molecule binds to the ssDNA template and makes the entire second strand without falling off even once). With one label, the process of the present invention can be carried out by watching the polymerase in real time with base pair resolution and identifying the sequence profile of that base, but without knowing the other bases. Therefore, using four different labels would be most desirable for greater speed and accuracy as noted above. However, information from measuring incorporation of nucleotides at a single molecule level, such as incorporation rates for individual bases in a given sequence context, can provide a means of further characterizing the sequence being synthesized. In respect to ensuring processive synthesis for the second operational mode of the present invention, accessory proteins can be utilized to make the nucleic acid/protein complex even more processive than using the nucleic acid polymerizing enzyme alone. For example, under optimal conditions, T7 DNA polymerase is processive over at least 10,000 bases, whereas in complex with the T7 helicase/primase protein, the processivity is increased to over 100,000 bases. Kelman et al., "Processivity of DNA Polymerases: Two Mechanisms, One Goal" *Structure* 6: 121–125 (1998), which is hereby incorporated by reference. A single-stranded binding protein is also a suitable accessory protein. Processivity is especially important at concentrations of nucleotide analogs that are below the saturation limit for a particular polymerase, because it is known that processivity values for polymerases are decreased at limiting substrate concentrations. See Patel et al., "Pre-Steady-State Kinetic Analysis of Processive DNA Replication Including Complete Characterization of an Exonuclease-Deficient Mutant," *Biochemistry* 30: 511–525 (1991), which is hereby incorporated by reference. Another possibility to ensure processivity is the development or discovery of a polymerase that is fully processive in the absence or at very low substrate concentrations (as is the case, e.g., for an elongating RNA polymerase/DNA complex). In case the processivity is not sufficiently high, it is possible to attach both the polymerase and the target nucleic acid molecule on the support proximate to each other. This would facilitate the reformation of the complex and continuation of DNA synthesis, in case the sequencing complex falls apart occasionally. Non-processive polymerases can also be used in accordance with the present invention for the case where the target nucleic acid is bound to the support. Here, the same or a different polymerase molecule can reform the complex and continue synthesis after dissociation of the complex.

Figure 6:
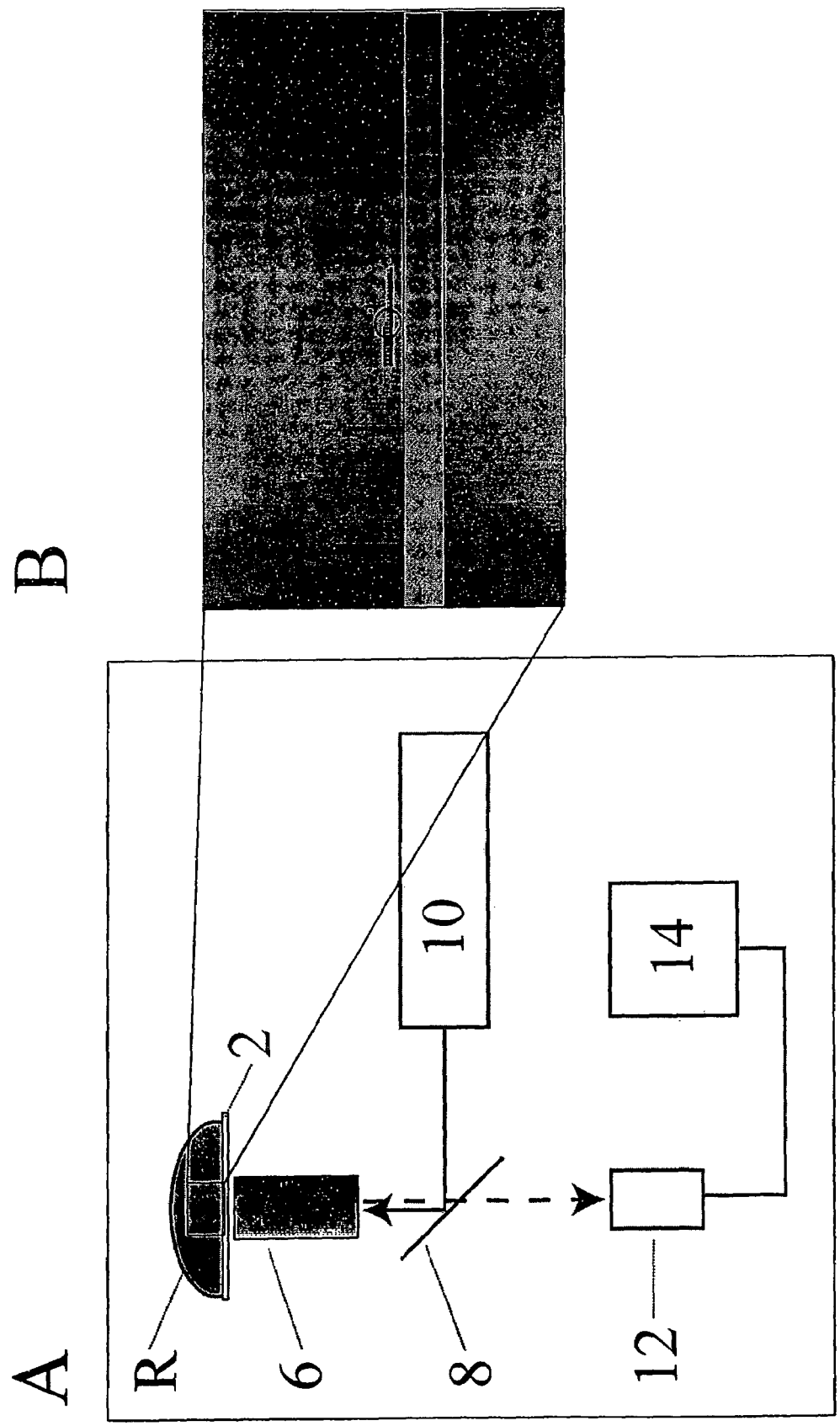
FIG. 6A shows a system for sequencing in accordance with the present invention.
FIG. 6B is an enlargement of a portion of that system.

One approach to carrying out the present invention is shown in FIG. 6. FIG. 6A shows a system for sequencing with reagent solution R positioned at surface 2 to which a primed target nucleic acid molecule complex is immobilized. By confining illumination to a small area proximate to the active site of polymerase extension, e.g. by focusing activating radiation with the help of lens or optical fiber 6, nucleotide analogs that become incorporated into the growing nucleic acid strand are detected, because they are located within the region of illumination. FIG. 6B shows an enlarged section of the device, with the polymerizing complex in the region of illumination. The substrate concentration is chosen such that the number of nucleotide analogs in the surrounding area in solution R are generally outside the illuminated region and are not detected.

As shown in FIG. 6A, illumination source 10 (e.g., a laser) directs excitation radiation by way of a dichroic beam splitter 8 through lens 6 and surface 2 to the immobilized primed target nucleic acid complex. This excites the label immobilized to the complex with the resulting emitted radiation passing back through surface 2 and lens or optical fiber 6. Dichroic beam splitter 8 allows passage of the emitted radiation to detector (or array of several detectors) 12 which identifies the type of emission. The detected emission information is then directed to computer 14 where the nucleotide base corresponding to the emission is identified and its identity stored. After multiple cycles of this procedure, the computer will be able to generate as output the sequence of the target nucleic acid molecule. The corresponding output of detection again corresponds to the scheme shown in FIG. 3, as explained above.

According to another embodiment of the present invention, illumination and detection of fluorescence may be achieved by making the support for the bound nucleic acid at the end of a first single-mode optical fiber carrying the excitation light. Either this and/or a second optical fiber may be used for collecting fluorescent photons. By transmitting the radiation of appropriate exciting wavelength through the first single-mode optical fiber, the label will fluoresce and emit the appropriate fluorescent light frequency. The emitted fluorescent light will be partially transmitted into the second optical fiber and separated spectrally such as by etched diffraction gratings on the fiber. The returned light spectrum identifies the particular bound nucleotide analog. Other techniques to deliver or collect light to the reaction site are conceivable, such as the use of waveguided illumination or evanescent wave illumination, such as total internal reflection illumination. One or several illumination sources, delivering one- or multiphoton excitation, can be employed. Suitable detectors include avalanche photodiode modules, photomultiplier tubes, CCD cameras, CMOS chips, or arrays or combinations of several detectors.

Because there is likely to exist an upper limit to the concentration of nucleotide analogs present in the observation volume that is correlated to a permissible signal to background ratio and the ability to distinguish the particular nucleotide analog that is being incorporated into nucleic acid from the nucleotide analogs that are just diffusing around the polymerase, it is possible that the sequencing procedure of the present invention must be carried out at concentrations below the saturating limit for one or more nucleotide analogs.

For example, if conventional diffraction limited optics is used for detection of fluorescence, the volume of observation is large so that substrate concentrations in the range of nanomolar would have to be used for an acceptable background signal. This is far below the usual $k_m$ of polymerases (usually in the range of µM), unless other means to reduce the background, such as lifetime discrimination as discussed above (FIG. 5), or volume confinement techniques, as described below, are utilized to either "electronically" or physically reduce background fluorescence contributions. In a conventionally focused laser beam, the focal volume is approximately 0.2 µm$^3$ (0.5 µm in diameter, 1.5 µm in the axial direction), corresponding to about 0.2 fl. In order for only one fluorescent nucleotide analog to be present on average in the excitation volume at any given time, the substrate concentration must be reduced to ca. 10 nM, a concentration far below the $k_m$ values of DNA polymerases (ca. 1–2 µM). See Polesky et al., "Identification of Residues Critical for the Polymerase-Activity of the Klenow Fragment of DNA-Polymerase-I from *Escherichia-coli*," *J. Biol. Chem.* 265:14579–14591 (1990) and McClure et al., "The Steady State Kinetic Parameters and Non-Processivity of *Escherichia coli* Deoxyribonucleic Acid Polymerase I," *J. Biol. Chem.* 250:4073–4080 (1975), which are hereby incorporated by reference. Thus, if the concentration of substrates is far below the $k_m$, processivity of nucleic acid synthesis has to be ensured by one of the above-mentioned possibilities. Alternatively, if the volume of observation can be reduced, a higher substrate concentration is permissible, which naturally increases processivity values. Therefore, one objective of the present invention is concerned with an effective reduction of the observation volume in order to reduce or prevent background fluorescence caused by labelled free nucleotides and increase processivity. This can be achieved in a number of ways.

One approach to reducing background noise involves electromagnetic field enhancement near objects with small radii of curvature.

Due to the so-called "antenna effect," electromagnetic radiation is strongly enhanced at the end of a sharp object, such as a metal tip. Using this procedure, the volume being enhanced roughly corresponds to a sphere with a diameter that is close to the diameter of the tip. This technique is disclosed in Sanchez, E. J., et al., "Near-Field Fluorescence Microscopy Based on Two-Photon Excitation with Metal Tips," *Phys. Rev. Lett.* 82:4014–17 (1999), which is hereby incorporated by reference.

In carrying out the process of the present invention, a nucleic acid polymerizing enzyme is positioned at the end of a metal tip with laser light being directed on it, e.g. with a conventional objective lens. Because the effective illuminated volume can now be on the order of the size of the polymerase itself, practically no fluorescence from the fluorescent nucleotides that are diffusing in the solution will be detected. Furthermore, the residence time of diffusing molecules through such a small volume is extremely short. However, incorporation of a fluorescent nucleotide will be seen as a relatively long burst of fluorescence, because that particular molecule will stay in this small illuminated volume (until it is removed as explained above).

Figure 7:
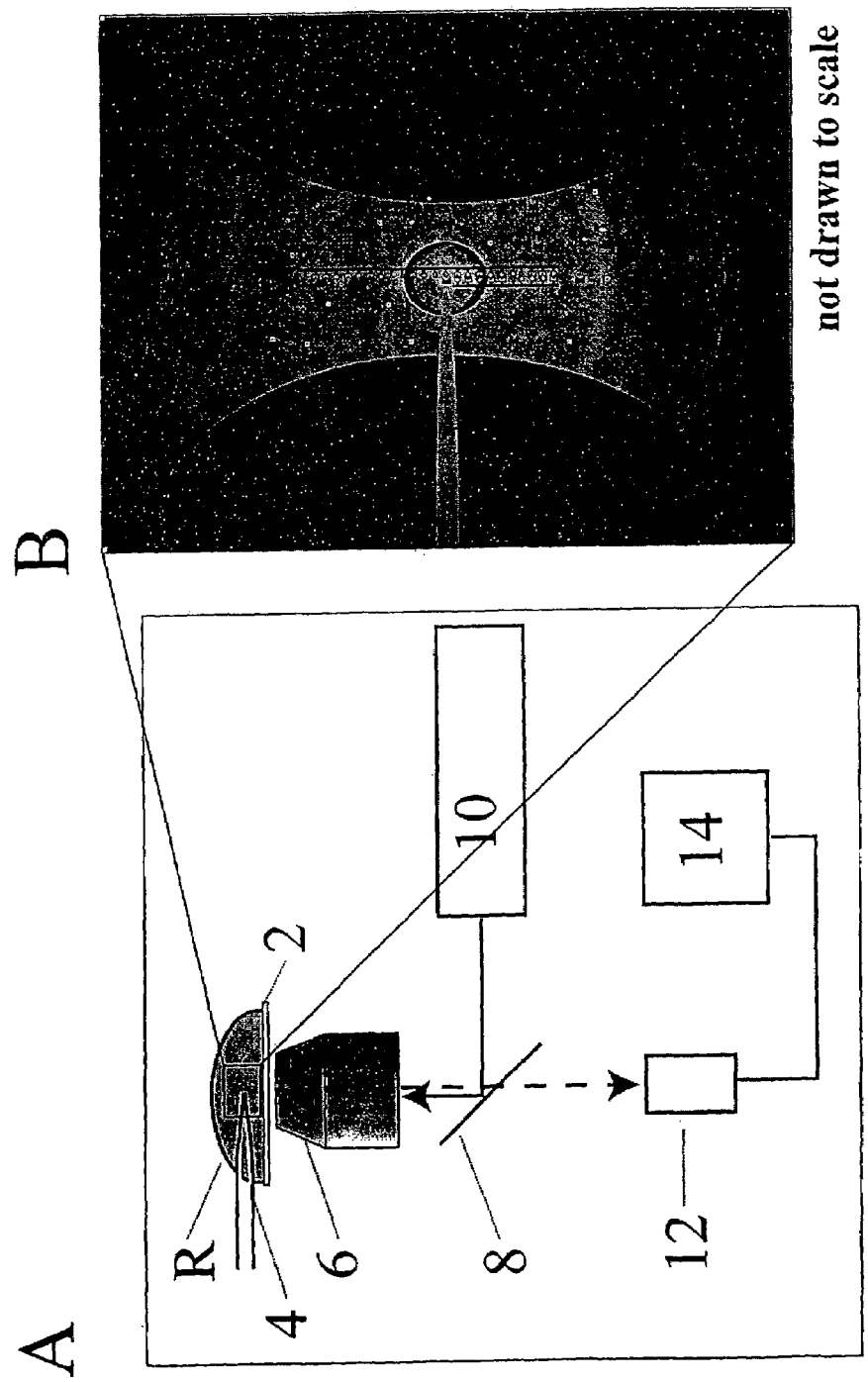
FIG. 7A shows a system for sequencing in accordance with the present invention using electromagnetic field enhancement with metal tips.
FIG. 7B is an enlargement of a portion of that system.

One approach to carrying out this embodiment of the present invention is shown in FIGS. 7A to B. FIG. 7A shows a system for sequencing with electromagnetic field enhancement with reagent solution R positioned at surface 2 to which a primed target nucleic acid molecule complex is immobilized. As shown in FIG. 7B, a metal tip carrying a polymerase is positioned in reagent solution R, creating a small region of illumination around the immobilized polymerase upon illumination by lens 6. By confining illumination to this small area, proximate to the active site of polymerase extension, nucleotide analogs that become incorporated into the growing nucleic acid strand are detected, because they are positioned within the region of illumination. On the other hand, nucleotide analogs in the surrounding area in solution R are generally outside this region and are not detected.

As shown in FIG. 7A, illumination source 10 (e.g., a laser) directs one or multiphoton excitation radiation with a nonzero polarization component parallel to the tip by way of a dichroic beam splitter 8 through lens 6 and surface 2 to the immobilized primed target nucleic acid complex. This excites the label immobilized to the complex with the resulting emitted radiation passing back through surface 2 and lens 6. Dichroic beam splitter 8 allows passage of the emitted radiation to detector 12 which identifies the type of emission. The detected emission information is then directed to computer 14 where the nucleotide base corresponding to the emission is identified and its identity stored. After multiple cycles of this procedure, the computer will be able to generate as output the sequence of the target nucleic acid molecule. The corresponding output of detection again corresponds to the scheme shown in FIG. 3, as explained above. The principal difference to the case discussed before is that the short peaks caused by randomly diffusing nucleotide analogs through the focal volume are now extremely short, because the volume of observation is so small. Therefore, this approach of reduction of observation volume also results in enhanced time resolution in respect to incorporated nucleotides versus unincorporated ones. This is true for all of the other possibilities of volume confinement discussed further below.

In carrying out this procedure, the tips can be formed from a variety of materials, e.g., metals such as platinum, silver, or gold. The fabrication of the tip can be accomplished, e.g., by electrochemical etching of wires or by ion-beam milling. See Sanchez, E. J., et al., "Near-Field Fluorescence Microscopy Based on Two-Photon Excitation with Metal Tips," *Phys. Rev. Lett.* 82:4014–17 (1999), which is hereby incorporated by reference.

The nucleic acid polymerizing enzyme can be attached to the end of the tip either by dipping the tip into a solution of nucleic acid polymerizing enzyme molecules, applying an electric field at the tip with charges attracting the nucleic acid polymerizing enzyme, or other techniques of coupling (e.g., with linkers, antibodies etc.). An alternative mode of using electromagnetic field enhancement for this scheme of sequencing is by positioning a bare tip in close proximity to an immobilized nucleic acid/nucleic acid polymerizing enzyme complex, rather than having the complex physically attached to the end of the tip. A population of complexes could, for example, be immobilized on a glass slide, and the tip is scanned over the surface until a useful complex for sequencing is found. Suitable techniques for carrying out this nanopositioning have been developed in the field of scanning probe microscopy.

Figure 8:
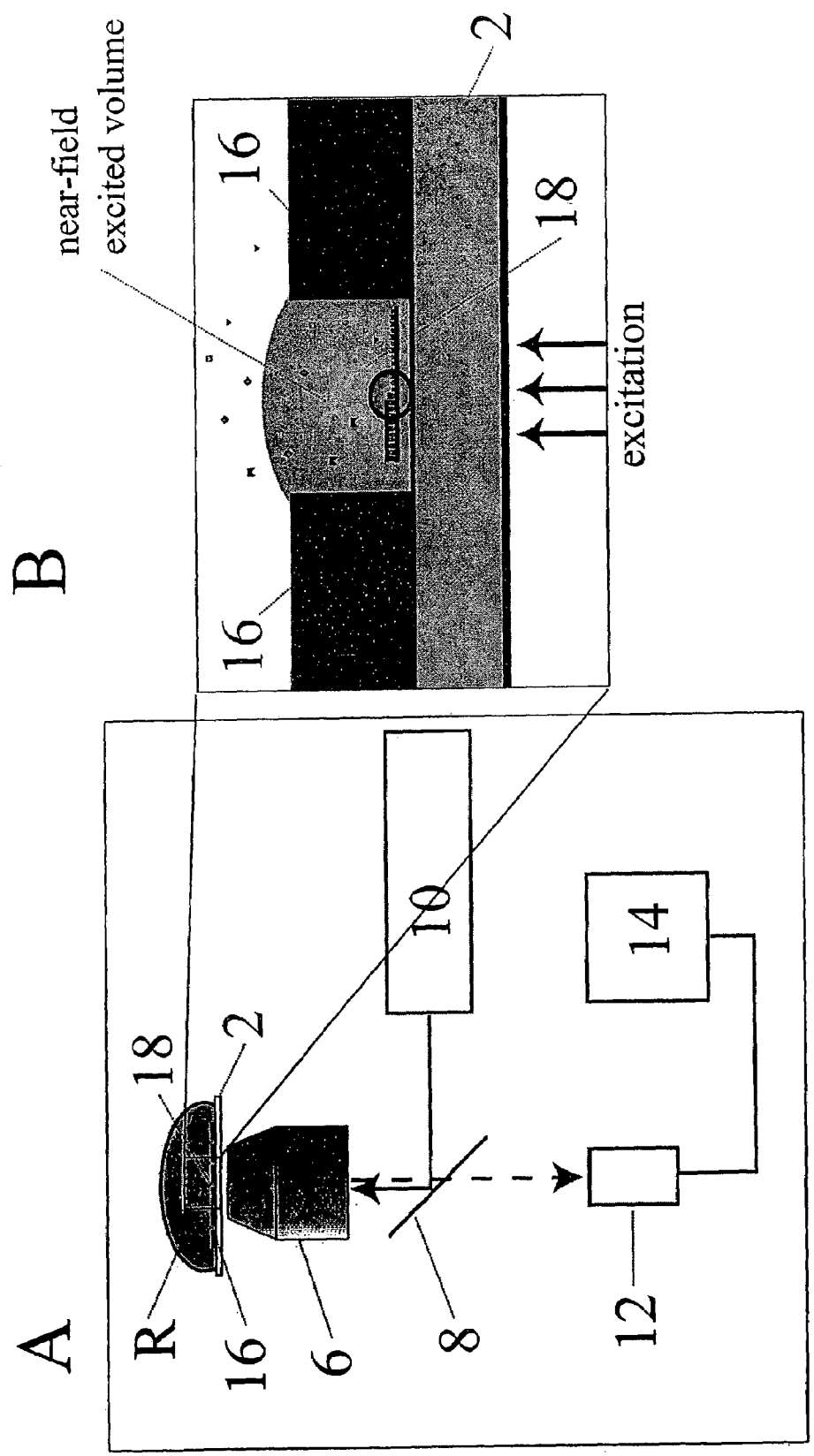
FIG. 8A shows a system for sequencing in accordance with the present invention using near field apertures.
FIG. 8B is an enlargement of a portion of that system.

Another approach for reducing background noise while carrying out the sequencing method of the present invention involves the use of near-field illumination, as shown in FIGS. 8A–B. Here, as depicted in FIG. 8B, the primed target nucleic acid complex is immobilized on surface 2 with opaque layer 16 being applied over surface 2. However, small holes 18 are etched into the opaque layer 16. When illuminated from below, the light cannot penetrate fully through the holes into reagent solution R, because the diameter of holes 18 is smaller than one half of the light's wavelength. However, there is some leakage which creates a small area of light right above surface 2 in hole 18, creating a so-called near-field excitation volume. As shown in FIG. 8B, the primed target nucleic acid complex is positioned in hole 18 where it is illuminated from below. By confining illumination to this small near-field area, incorporated nucleotide analogs, positioned within the region of illumination, are detected. On the other hand, the quantity of nucleotide analogs which do not serve to extend the primer are few in number due to the small size of hole 18 and, to the small extent detected, are easily distinguished from incorporated nucleotide analogs as described above.

The system for carrying out this embodiment is shown in FIG. 8A. Illumination source 10 (e.g., a laser) directs excitation radiation by way of dichroic beam splitter 8 through lens 6 and surface 2 to the immobilized primed target nucleic acid complex. This excites the label immobilized to the complex with the resulting emitted radiation passing back through surface 2 and lens 6. Dichroic beam splitter 8 allows passage of the emitted radiation to detector 12 which identifies the type of emission. The detected emission information is then directed to computer 14 where the nucleotide base corresponding to the emission is identified and its identity stored. After multiple cycles of this procedure, the computer will be able to generate as output the sequence of the target nucleic acid molecule.

As a suitable alternative using near-field excitation volumes, the near-field volume can also be generated by the use of one or many tapered optical fibers commonly used in scanning near-field microscopy.

Nanofabrication is another technique useful in limiting the reaction volume to reduce the level of background fluorescence. This involves confinement of the excitation volume to a region within a nanochannel. Here, confinement is possible in two of three spatial dimensions. A reaction vessel with a volume much smaller than focal volumes attainable with far-field focusing optics is fabricated on a silicon or fused silica wafer from optically transparent materials. Turner et al., "Solid-State Artificial Gel for DNA Electrophoresis with an Integrated Top Layer," *Proceedings of SPIE: Micro-and Nano-Fabricated Structures and Devices for Biomedical Environmental Applications* 3258: 114–121 (1998), which is hereby incorporated by reference. The technique takes advantage of a polysilicon sacrificial layer to define the working cavity of the channels. Stern et al., "Nanochannel Fabrication for Chemical Sensors," *J. Vac. Sci. Technol.* B15:2887–2891 (1997) and Chu et al., "Silicon Nanofilter with Absolute Pore Size and High Mechanical Strength," *Proc. SPIE—Int. Soc. Opt. Eng. (USA)* 2593: 9–20 (1995), which are hereby incorporated by reference. The floor, ceiling, and walls of the channels are made of silicon nitride, which is deposited conformally over a patterned polysilicon sacrificial layer. The sacrificial layer is then removed with a high-selectivity wet chemical etch, leaving behind only the silicon nitride. This technique has demonstrated precise critical dimension (CD) control over a wide range of structure sizes. The height of the polysilicon layer can be controlled to within 5 nm over an entire device, and the lateral dimensions are limited in size and CD control only by the lithography technique applied. The nanostructure can have a punctuate, acicular, or resonant configuration to enhance label detection.

Figure 9:
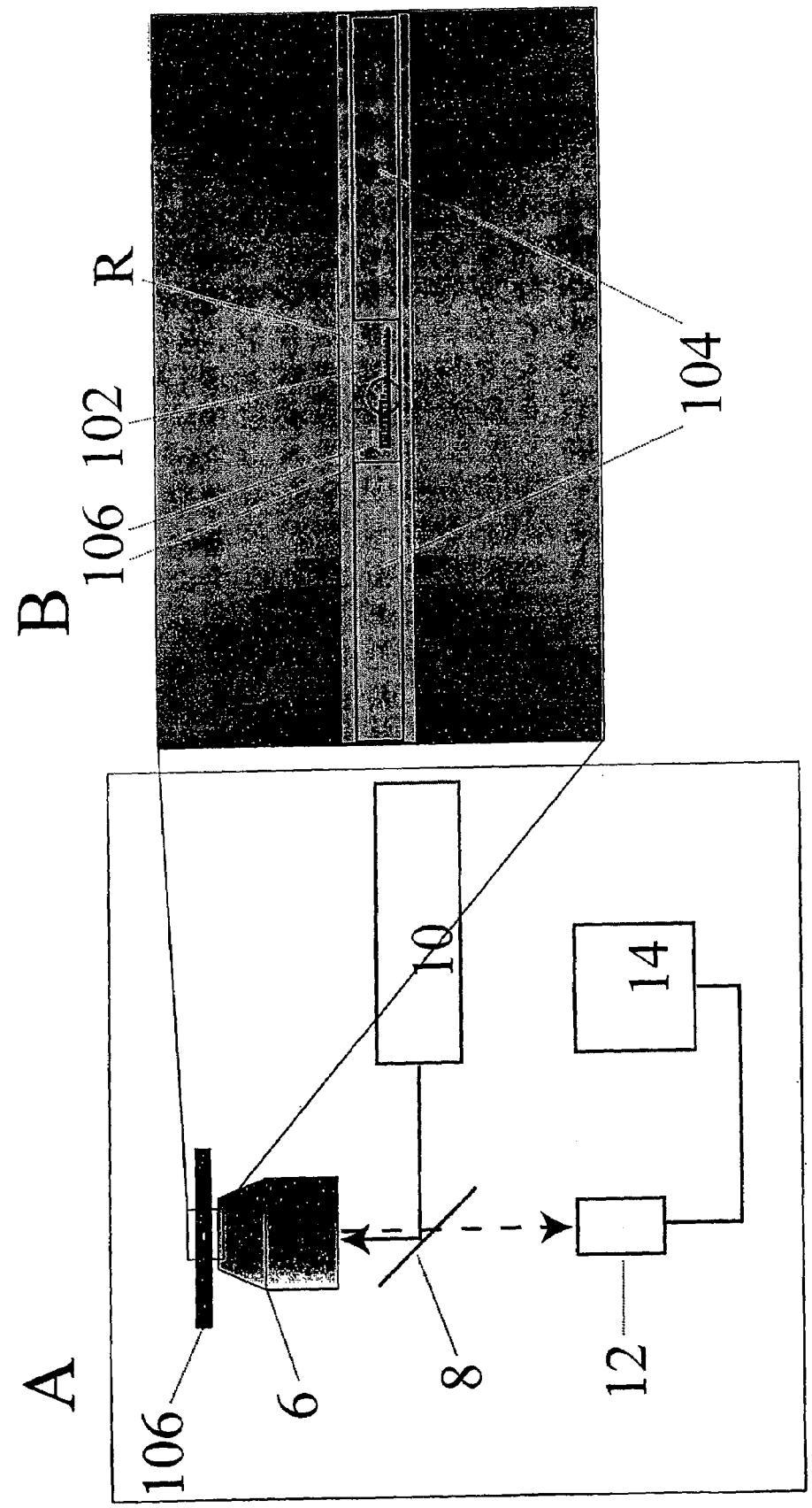
FIG. 9A shows a system for sequencing in accordance with the present invention using nanochannels.
FIG. 9B is an enlargement of a portion of that system.

FIGS. 9A–B show a nanofabricated system in accordance with the present invention. Shown in FIG. 9B is an enlarged view of the cross-section of the nanochannel, with reagents R located only in confined area 102, which is created by the channel walls 104 and 106. The primed target nucleic acid molecule complex is positioned within confined area 102. As a result, when excitation light passes through confined area 102, the label of the incorporated nucleotide analog is excited and emits radiation which is detected and identified as corresponding to a particular nucleotide base added to the sequence of the extending primer. By passing the reagents through confined area 102, the quantity of nucleotide analogs which do not extend the primer are few in number at any particular point in time. To the small extent such mobile entities are detected, they are easily distinguished from immobilized moieties as described above.

FIG. 9A shows a system for carrying out the nanochannel embodiment of the present invention. Illumination source 10 (e.g., a laser) directs excitation radiation by way of dichroic beam splitter 8 through lens 6 and nanochannel 106 to the immobilized primed target nucleic acid complex. This excites the label immobilized to the complex with the resulting emitted radiation passing back through lens 6. Dichroic beam splitter 8 allows passage of the emitted radiation to detector 12 which identifies the type of emission. The detected emission information is then directed to computer 14 where the nucleotide base corresponding to the emission is identified and its identity stored. After multiple cycles of this procedure, the computer will be able to generate as output the sequence of the target nucleic acid molecule.

FIGS. 10A–B show systems for supplying reagents to a nanofabricated confinement system in accordance with the present invention. In FIG. 10A, the reagents, which include dATP, dCTP, dGTP, dUTP, the nucleic acid source, and buffer are held in separate reservoirs and connected through separate conduits to manifold 200 where the reagents are mixed together before entering nanochannel 202. The components of this system upstream and downstream of nanochannel 202 can be combined as a microstructure. In the process of passing rapidly through nanochannel 202, the reagents move rapidly through reaction zone 204 where the sequencing procedure of the present invention is carried out. From nanochannel 202, the residual reagents R pass through outlet 206. The system of FIG. 10B is generally similar to that of FIG. 10A, but the former system is on a single chip with pads to connect the system to fluid reservoirs. In particular, the reservoir for each of the reagents is coupled to the chip 208 via inlet pads 210a–f, while the outlet for discharged reagents is connected to pad 212.

Nanofabricated channels of 75 nm width and 60 nm height have been manufactured with excellent optical transparency and used for DNA flow control. See Turner et al., "Solid-State Artificial Gel for DNA Electrophoresis with an Integrated Top Layer," *Proceedings of SPIE: Micro-and Nano-Fabricated Structures and Devices for Biomedical Environmental Applications* 3258:114–121 (1998), which is hereby incorporated by reference. By placing the nucleic acid synthesis complex into a channel of depth z=25 nm, minimizing the x-dimension of the focused laser beam to ca. 300 nm, and fixing the y-dimension by the channel width at 100 nm, the effective volume of observation can be reduced to $7.5 \times 10^{-4}$ μm³, corresponding to 0.75 attoliters. Here, the concentration for only one substrate molecule to be present in the excitation volume amounts to 2 μM, a substrate concentration well within the range of rapid and efficient nucleic acid polymerization. Moreover, since there are four different nucleotide analogs, each to be distinguished, the effective substrate concentration for the polymerase is four times higher. If a smaller effective volume of observation is required, the y-dimension in the flow direction can be reduced to about 100 nm by illumination with the interference pattern of two objectives at about 90° axial angles as in theta microscopy. See Stelzer et al., "A New Tool for the Observation of Embryos and Other Large Specimens: Confocal Theta Fluorescence Microscopy," *J. Microscopy* 179: 1–10 (1995), which is hereby incorporated by reference.

To excite the labels, activating energy is focused proximate to the active site of polymerase extension (i.e. where the polymerase is located). To the extent this active site moves during extension (e.g., as a result of movement by the polymerase), the focus of the activating energy is also moved.

A necessary consideration is the choice between one-photon and multiphoton excitation of fluorescence. Multiphoton excitation provides some powerful advantages, but it is more complex and more expensive to implement. Multiphoton excitation fluorescence utilizing simultaneous absorption of two or more photons from bright, femtosecond infrared pulses generated by ultrafast solid state mode locked lasers provides the most promising approach. See Denk et al., "2-Photon Laser Scanning Fluorescence Microscopy," *Science* 248:73–76 (1990), which is hereby incorporated by reference. Sensitivity to single molecule fluorescence is routinely obtained and is temporally resolvable to the microsecond level with fluorescence lifetimes measurable with reasonable accuracy for single molecules. See Mertz et al., "Single-Molecule Detection by Two-Photon-Excited Fluorescence," *Optics Lett.* 20:2532–2534 (1995) and Eggeling et al., "Monitoring Conformational Dynamics of a Single Molecule by Selective Fluorescence Spectroscopy," *Proc. Natl. Acad. Sci. USA* 95:1556–1561 (1998), which are hereby incorporated by reference.

The ideal fluorescent signal for single molecule sequencing consists of time resolved bursts of distinguishable fluorescence as each nucleotide is bound. Thus, in the ideal situation, a time-resolved train of color resolved fluorescent bursts could be obtained if nucleotides were bound at distinguishable intervals as described in FIG. 3. Full resolution of the time sequence of events therefore offers the best background reduction and reliable possibility for nucleotide recognition. Since Keith the currently available polymerases, labelled nucleotides are most likely added no faster than at 1 millisecond intervals, it should be possible that all of the detected fluorescence photons from each labelled nucleotide can be accumulated and removed before the next fluorescent nucleotide is bound. This ideal burst-gap-burst sequence is realized although actually every molecular kinetic step of polymerization involves the stochastic Poisson process. For a single Poisson process, the most probable time delay between events is zero although the average delay would be larger than zero. However, the process of incorporation of a single dNTP into DNA by DNA polymerase is a sequential multistep process of at least 5 different events. See Patel et al., "Pre-Steady-State Kinetic Analysis of Processive DNA Replication Including Complete Characterization of an Exonuclease-Deficient Mutant," *Biochemistry* 30: 511–525 (1991). The sequential summation of these steps will result in a most likely time delay larger than zero. Therefore, the photon bursts are not very likely to overlap.

For conventional fluorophores, about $10^5$ photons per fluorophore will be emitted before photobleaching. Detection of (at most) 1% of the emission yields about $10^3$ photons for a relative noise uncertainty of 3%. Background due to free nucleotides is reduced to a nearly negligible level by the schemes discussed above, e.g., by limiting the size of the focal volume to contain only about one free labelled nucleotide, with very short dwell times.

The expected detection level is about $10^3$ photons from each labelled nucleotide, in about $10^{-3}$ s. This is an acceptable counting rate, $\sim 10^6$ Hz, and an acceptable fluorophore excitation rate at about one tenth of singlet excited state saturation. This fluorescence excitation creates a detected burst of $\sim 10^3$ photons in about 1 ms at the characteristic wavelength for each labelled nucleotide, leaving, on average, a gap of about 1 ms before the next nucleotide is added, well within the average time intervals between nucleotide addition at probably more than one millisecond. Possible burst overlaps can be analyzed and resolved by the analytical treatment of continuous measurements of data in time coherent sequences in (at best) 4 channels for most accurate sequencing results. With the photon statistics available in the experimental design and recently developed coupled multi-channel analyzers and operational software, error rates can be made acceptable with 4 labelled nucleotides or with the strategies involving a smaller number of labels as outlined above.

Spectral resolution of four fluorophores identifying the nucleotides can be achieved with two-photon excitation by infrared pulses. All 4 fluorophores can be simultaneously excited due to the wide excitation bands usually characteristic of two-photon excitation. See Xu et al., "Multiphoton Excitation Cross-Sections of Molecular Fluorophores," *Bioimaging* 4:198–207 (1996), which is hereby incorporated by reference. Alternatively, multiple excitation sources can be used in combination or by fast switching to illuminate the sequencing complex if necessary. Spectral separation is accomplished with conventional interference filters but emission spectra may overlap, complicating the time correlation analysis and perhaps requiring cross correlation of the 4 color channels for correction. If compatibility of fluorophores with the nucleic acid polymerizing enzyme limits the applicability of suitable dye sets, a combination of techniques can be applied to distinguish the labels.

Another potential way to distinguish incorporation of a nucleotide into the growing nucleic acid strand consists of measuring changes in fluorescence lifetime. Fluorescence lifetime of an oligonucleotide pyrene probe has been observed to vary in a sequence-dependent manner upon DNA attachment. See Dapprich J, "Fluoreszenzdetection Molekularer Evolution (Fluorescence Detection of Molecular Evolution)," Dissertation, Georg-August-Univ., Goettingen, Germany (1994), which is hereby incorporated by reference. Photophysical interactions between the fluorophore and the base result in characteristic fluorescence decay times, and can also be used to differentiate the bases, as discussed above. Lifetime determination and discrimination on the single molecule level has recently been demonstrated so that discrimination between bases being incorporated and freely diffusing nucleotides could be carried out by fluorescence lifetime measurements. See Eggeling et al., "Monitoring Conformational Dynamics of a Single Molecule by Selective Fluorescence Spectroscopy," *Proc. Natl. Acad. Sci. USA* 95:1556–1561 (1998), which is hereby incorporated by reference.

Time correlated measurements in four fluorescence wavelength channels can be used effectively in carrying out the process of the present invention. Overlap of emission spectra may allow signals from one fluorophore to enter several channels but the relative count rate and timing identifies the label correctly. Simultaneous signals from an incorporated labelled nucleotide and a free label are distinguishable by the time duration and magnitude of the bursts, which are limited for the free label. Label ambiguity can be further reduced by utilization of fluorescence decay time measurements which can be realized with the available 0.1 ns resolution of time delays for fluorescence photon emission after each femtosecond laser excitation pulse. The fluorescence photon emission and photobleaching processes themselves are also stochastic processes but involve sufficiently disparate quantum efficiencies that error rates should be negligible.

In rejecting background from the freely diffusing or flowing labelled nucleotides, the very short dwell time of any individual free nucleotide in the focal volume is advantageously used. The characteristic diffusion time for a free nucleotide analog across the open dimension of the focal volume (in the worst case of non-interferometric far-field illumination) will be $\tau_D \sim y^2/4D \sim 2 \times 10^{-5}$ sec, with y being the focal volume dimension and D the diffusion coefficient. An iontophoretic flow velocity of 1 cm/s is sufficient to keep its short bursts of fluorescence to less than $10^{-5}$ sec and reduce the photon numbers by an order of magnitude. This will assure discrimination against free nucleotides and identify the time series of bursts representing the nucleic acid sequence, provided the nucleotide analog concentrations are appropriately low as discussed. Magde et al., "Thermodynamic Fluctuations in a Reacting System—Measurement by Fluorescence Correlation Spectroscopy," *Phys. Rev. Lett.* 29:705–708 (1972) and Maiti et al., "Measuring Serotonin Distribution in Live Cells with Three-Photon Excitation," *Science* 275:530–532 (1997), which are hereby incorporated by reference. Discrimination can be improved by utilizing volume confinement techniques or time-gated detection, as discussed above.

Detection of fluorescence resonance energy transfer (FRET) from a donor fluorophore (e.g., a donor attached to the polymerase) to adjacent nucleotide analog acceptors that are incorporated into the growing nucleic acid strand suggests a further elegant possibility of lowering background from incorporated nucleotides. FRET only reaches very short distances including about 20 nucleotides and decays at the reciprocal sixth power of distance. The excited donor molecule transfers its energy only to nearby acceptor fluorophores, which emit the spectrally resolved acceptor fluorescence of each labelled nucleotide as it is added. Already incorporated nucleotides farther away from the donor would not contribute to the fluorescent signal since distance and orientation constraints of energy transfer reduce the effective range of observation to less than 60 Å, thereby effectively eliminating background fluorescence from unincorporated nucleotides. Without photobleaching, the method requires high sensitivity since repeat nucleotides leave the range of FRET at the same rate that new nucleotides are added, possibly creating sequence recognition ambiguity. Photobleaching or photochemical cleavage, or their combination as discussed above could resolve the problem. Photobleaching of the donor molecules using FRET can be avoided if it is the template nucleic acid that is attached and the donor bearing nucleic acid polymerizing enzyme is periodically replaced.

A final important consideration for the success of the present invention concerns the stability of the protein/nucleic acid complex in activating radiation, such as tightly focussed laser beams. It is not expected that the enzyme is affected by the excitation illumination, because wavelengths are chosen at which proteins do not absorb, the stability of the polymerase in the laser beam should be sufficiently high to allow for accurate sequencing runs over long read lengths. Previous investigations exposing enzymes to strong laser light have examined photodamage and loss of function. Immobilized RNA polymerase/DNA complexes showed inactivation times of 82±58 s for 1047 nm Nd:Y laser light of 82 to 99 mW laser power focused at the protein, corresponding to intensities of approximately $10^8$ W/cm$^2$. Other studies on the actomyosin or kinesin systems indicated similar stability. Both DNA and biotin-avidin linkages have been shown to be photostable in optical traps. See Yin et al., "Transcription Against an Applied Force," *Science* 270: 1653–1657 (1995), Svoboda et al. "Direct Observation of Kinesin Stepping by Optical Trapping Interferometry," *Nature* 365: 721–727 (1993), and Molloy et al., "Movement and Force Produced by a Single Myosin Head" *Nature* 378: 209–212 (1995), which are hereby incorporated by reference. For fluorescence detection of nucleotide analogs according to the present invention, laser powers (intensities) typical of FCS measurements are expected, on the order of 0.1 mW ($10^5$ W/cm$^2$) for one-photon and 1 mW ($10^{6-107}$ W/cm$^2$) for two-photon excitation, thereby being significantly lower than in the case of optical tweezers described above. Enzyme stability should therefore be higher, moreover, with the rapid speed of sequencing proposed by this method (e.g., 100 bp/s), even 80 s are sufficient to determine the sequence of 8 kb nucleic acid.

Although the invention has been described in detail for the purposes of illustration, it is understood that such detail is solely for that purpose, and variations can be made therein by those skilled in the art without departing from the spirit and scope of the invention which is defined by the following claims.

What is claimed:

1. A single-step method for sequencing a plurality of target nucleic acid molecules, said method comprising subjecting the plurality of target nucleic acid molecules to a polymerization reaction with a plurality of types of nucleotides or nucleotide analogs to yield a population of growing nucleic acid strands that are complementary to their respective target nucleic acid molecules, wherein the target nucleic acid molecule and/or the nucleic acid polymerization enzyme is attached to a support; and optically identifying a time sequence of incorporation of said plurality of types of nucleotides or nucleotide analogs into at least two growing nucleic acid strands in said population, wherein the time sequence for each of said at least two growing nucleic acid strands is different.

2. A method for sequencing a plurality of target nucleic acid molecules, said method comprising:

subjecting the plurality of target nucleic acid molecules to a polymerization reaction in the presence of a plurality of types of nucleotides or nucleotide analogs to yield a population of growing nucleic acid strands that are complementary to their respective target nucleic acid molecules, wherein the target nucleic acid molecule and/or the nucleic acid polymerization enzyme is attached to a support; and optically identifying in real-time a time sequence of incorporation of a plurality of types of nucleotides or nucleotide analogs into at least two growing nucleic acid strands in said population.

3. A method according to claims 1 or 2, wherein the polymerization reaction is performed by a nucleic acid polymerizing enzyme selected from the group consisting of a DNA polymerase, an RNA polymerase, reverse transcriptase, and mixtures thereof.

4. A method according to claim 3, wherein the nucleic acid polymerizing enzyme is a thermostable polymerase or a thermodegradable polymerase.

5. A method according to claim 1, wherein the target nucleic acid molecules are selected from the group consisting of double-stranded DNA, single-stranded DNA, single stranded DNA hairpins, DNA/RNA hybrids, RNA with a recognition site for binding of the polymerase, and RNA hairpins.

6. A method according to claim 1, wherein the nucleotide analogs are selected from the group consisting of a ribonucleotide, a deoxyribonucleotide, a modified ribonucleotide, a modified deoxyribonucleotide, a peptide nucleotide, a modified peptide nucleotide, and a modified phosphate-sugar backbone nucleotide.

7. A method according to claim 1, wherein the nucleotides or nucleotide analogs further comprise a label.

8. A method according to claim 7, wherein the label is selected from the group consisting of chromophores, fluorescent moieties, enzymes, antigens, dyes, phosphorescent groups, chemiluminescent moieties, scattering or fluorescent nanoparticles and Raman signal generating moieties.

9. A method according to claim 7, wherein the label is attached to the nucleotides or nucleotide analogs at a base, sugar moiety, alpha phosphate, beta phosphate, or gamma phosphate of the nucleotides or nucleotide analogs.

10. A method according to claim 7, wherein each of the plurality of types of nucleotides or nucleotide analogs have different labels which are distinguished from one another during said identifying.

11. A method according to claim 7, wherein three or less of the plurality of types of nucleotides or nucleotide analogs have a different label.

12. A method according to claim 7, wherein the different types of nucleotides or nucleotide analogs have the same label but are distinguished by different properties due a presence of base fluorophores, quenched fluorophores, or fluorogenic nucleotides or nucleotide analogs.

13. A method according to claims 3, wherein the nucleic acid polymerizing enzyme carries a label and said identifying is carried out by detecting interaction between the label and the nucleotide analog.

14. A method according to claim 13, wherein the label is a fluorescence resonance energy transfer donor or acceptor.

15. A method according to claims 1 or 2, wherein said identifying is carried out by optical procedures selected from the group consisting of far-field microspectroscopy, near-field microspectroscopy, evanescent wave or wave guided illumination, nanostructure enhancement, and combinations thereof.

16. A method according to claims 1 or 2, wherein said identifying is carried out by single photon excitation, multiphoton excitation, fluorescence resonance energy transfer, or photoconversion or a combination thereof.

17. A method according to claims 1 or 2, wherein said identifying is performed by spectral wavelength discrimination, measurement and separation of fluorescence lifetimes, fluorophore identification, background suppression or a combination thereof.

18. A method according to claim 17, wherein fluorophore identification or background suppression utilizes fast switching between excitation modes and illumination sources, and combinations thereof.

19. A method according to claims 1 or 2, wherein said plurality of target nucleic acids are attached to a support.

20. The method of claims 1 or 2, wherein each target nucleic acid is hybridized to a separate oligonucleotide which is attached to a support.

21. The method of claim 3 wherein said DNA polymerizing enzyme is attached to a support.

22. A method according to claims 1 or 2, wherein said identifying is carried out by reducing background noise resulting from free nucleotides or nucleotide analogs.

23. A method according to claim 1, wherein the nucleotides or nucleotide analogs comprise labels attached to the 5' termini of the nucleotides or analogs.

24. A method according to claim 23, wherein said identifying is effected by detecting the labels attached to the nucleotides or nucleotide analogs.

* * * * *

UNITED STATES PATENT AND TRADEMARK OFFICE
CERTIFICATE OF CORRECTION

| | | |
|---|---|---|
| PATENT NO. | : 7,033,764 B2 | Page 1 of 1 |
| APPLICATION NO. | : 11/014015 | |
| DATED | : April 25, 2006 | |
| INVENTOR(S) | : Korlach et al. | |

It is certified that error appears in the above-identified patent and that said Letters Patent is hereby corrected as shown below:

In the Specification at column 1, line 12, please insert, as a new paragraph:

-- This invention was made with funds provided by the U.S. Government under National Science Foundation Grant No. BIR8800278, and National Institutes of Health Grant No. P412RR04224-11, and Department of Energy Grant No. DE-FG02-99ER62809. The U.S. Government has certain rights in this invention. --

In claim 13, at column 28, line 59, please change:

"claims" to -- claim --

Signed and Sealed this

Twenty-seventh Day of July, 2010

David J. Kappos
*Director of the United States Patent and Trademark Office*